United States Patent [19]

Nakahama et al.

[11] Patent Number: 5,770,438
[45] Date of Patent: Jun. 23, 1998

[54] PROCESS FOR ENANTIOSELECTIVE HYDROLYSIS OF α-(2-AMINO)-PHENYL-BENZENEMETHANOL ESTER TYPE COMPOUNDS USING BACILLUS, PSEUDOMONAS OR STREPTOMYCES

[75] Inventors: Kazuo Nakahama, Kyoto; Motowo Izawa, Hyogo; Yoichi Nagano, Osaka; Naoki Tarui, Osaka; Kiyoharu Matsumoto, Osaka; Masakuni Kori, Hyogo; Tsuneo Kanamaru; Toshiaki Nagata, both of Osaka, all of Japan

[73] Assignee: Takeda Chemical Industries, Ltd., Osaka, Japan

[21] Appl. No.: 550,643

[22] Filed: Oct. 31, 1995

[30] Foreign Application Priority Data

Nov. 1, 1994 [JP] Japan .................................. 6-269056
Mar. 7, 1995 [JP] Japan .................................. 7-047156

[51] Int. Cl.$^6$ ................................................. C12P 41/00
[52] U.S. Cl. ............................................................. 435/280
[58] Field of Search .................................... 435/280, 839, 435/874, 886, 128

[56] References Cited

FOREIGN PATENT DOCUMENTS

| 0567026 | 10/1993 | European Pat. Off. . |
| 0645377 | 3/1995 | European Pat. Off. . |
| 0645378 | 3/1995 | European Pat. Off. . |
| 3-22992 | 1/1991 | Japan . |
| WO90/04643 | 5/1990 | WIPO . |
| WO 21834 | 8/1995 | WIPO . |

OTHER PUBLICATIONS

Okumura S et al., BBA 575:156–65 (1979).
Hills M et al, BBA 1042:237–240 (1990).

*Primary Examiner*—Sandra E. Saucier
*Attorney, Agent, or Firm*—Fitzpatrick, Cella, Harper & Scinto

[57] ABSTRACT

A process for producing an optically active form of a compound of formula (I)

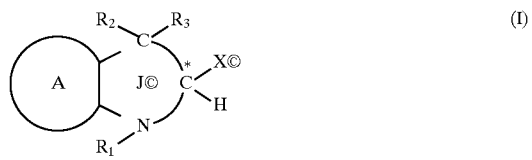

wherein $R_1$ represents hydrogen or a hydrocarbon group that may be substituted; $R_2$ and $R_3$ independently represent hydrogen, a hydrocarbon group that may be substituted, or a heteroaromatic group that may be substituted; X' represents a substituent comprising an esterified carboxyl group or an acylated hydroxyl group; ring A represents a benzene ring that may be substituted or a heteroaromatic ring that may be substituted; ring J' represents a 7- or 8-membered heterocyclic ring containing at most 3 hetero-atoms as ring-constituent members, which may have a further substituent or substituents in addition to $R_1$, $R_2$, $R_3$ and X', and C* denotes a chiral carbon atom or a salt thereof, which comprises subjecting the racemic compound of the formula (I) or a salt thereof, or alternatively a racemic starting compound for synthesizing the compound of the formula (I) to enzymatically enantioselective hydrolysis to provide an optically active form thereof.

9 Claims, 2 Drawing Sheets

PROCESS FOR ENANTIOSELECTIVE HYDROLYSIS OF α-(2-AMINO)-PHENYL-BENZENEMETHANOL ESTER TYPE COMPOUNDS USING BACILLUS, PSEUDOMONAS OR STREPTOMYCES

FIELD OF THE INVENTION

This invention relates to a process for producing optically active compounds. More particularly, this invention relates to a process for producing optically active compounds having plasma cholesterol and triglyceride lowering activities. This invention also relates to a process for producing optically active benzhydrol derivatives, which are useful for synthesizing the above compounds as well as a variety of other optically active compounds.

BACKGROUND OF THE INVENTION

It is of importance that a racemate or a mixture of dextrorotatory and levorotatory isomers be optically resolved into the component isomers because the isomer having useful pharmacological activity generally is either the dextrorotatory component (d-form) or the levorotatory component (l-form).

Moreover, when a high optical purity is valued, the racemic material is desirably fractionated efficiently into dextrorotatory and levorotatory components.

Meanwhile, EPA Laid-open No. 567026, WO95/21834 (based on JP Application Laid-open No. 15531/1994), EPA Laid-open No. 645377 (JP Application Laid-open No. 229159/1994) and EPA Laid-open No. 645378 (based on JP Application Laid-open No. 229160/1994) describe compounds having squalene synthase inhibitory activity and being, therefore, of value as plasma cholesterol lowering agents. There have not been known, however, any advantageous methods for obtaining these optically active compounds enzymatically, for example, with the use of microorganisms.

On the other hand, because optically active forms of benzhydrol derivatives are of value as intermediates for the production of drugs and farm chemicals, development of an economical process for their production has been awaited. Among the known production processes for optically active forms of benzhydrol derivatives are the optical resolution process utilizing L-tartaric acid and the process involving chiral reduction of a benzophenone with the aid of a microorganism [JP Laid-open No. 22992/1991, Chem. Pharm. Bull. 39, 2498 (1991)].

SUMMARY OF THE INVENTION

Figure 1:
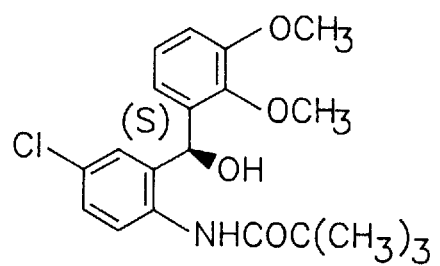
FIG. 1 shows the result of X-ray crystallographic structure analysis.
Figure 1:
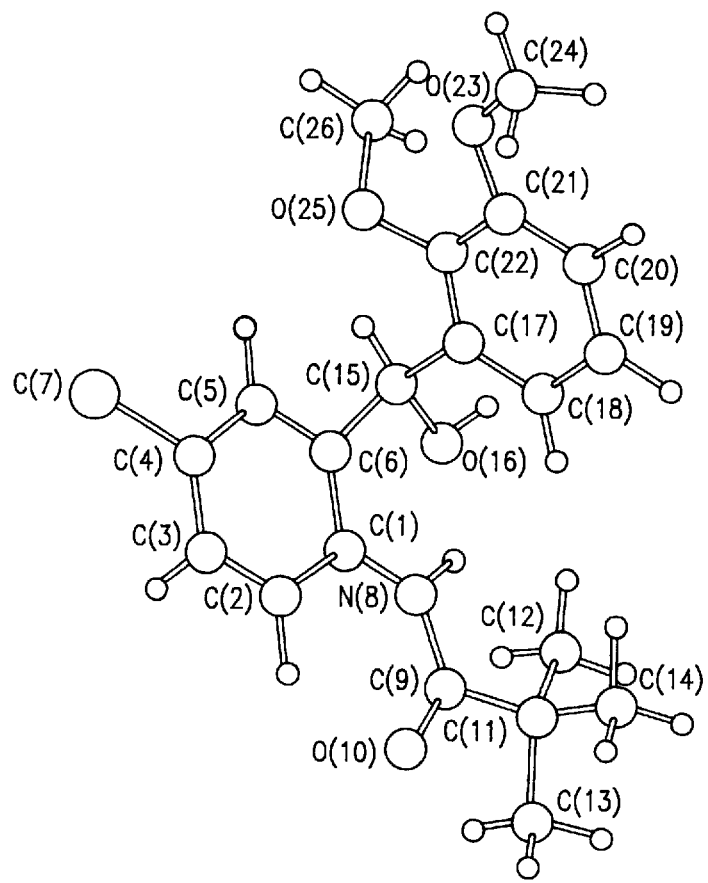

This invention provides an efficient process for producing an optically active form of a compound of the formula (I):

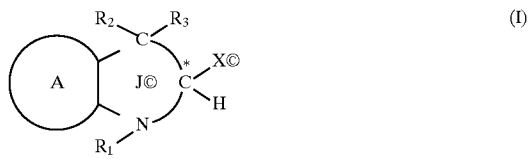

wherein $R_1$ represents hydrogen or a hydrocarbon group that may be substituted; $R_2$ and $R_3$ independently represent hydrogen, a hydrocarbon group that may be substituted, or a heteroaromatic group that may be substituted; X' represents a substituent group comprising an esterified carboxyl group or an acylated hydroxyl group; ring A represents a benzene ring that may be substituted or a heteroaromatic ring that may be substituted; ring J' represents a 7- or 8-membered heterocycle containing at most 3 hetero-atoms as ring-constituent members, which may have a further substituent or substituents in addition to $R_1$, $R_2$, $R_3$ and X' and C* denotes a chiral carbon atom or a salt thereof, which comprises subjecting the racemic compound of the formula (I) or a salt thereof or the racemic compound of the starting compound for synthesizing the compound of the formula (I) to enzymatic enantioselective hydrolysis to provide an optically active form thereof.

DETAILED DESCRIPTION OF THE INVENTION

The inventors of this invention investigated the possibility of microbial optical resolution of an acetic acid ester involving the chiral carbon atom of a ring system represented by the formula:

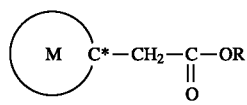

wherein ring M is a heterocyclic ring system containing a chiral carbon atom as a ring member; R represents a substituent group; and C* denotes a chiral carbon atom. After extensive research, the inventors discovered that when a culture broth from a strain of microorganism capable of catalyzing enantioselective hydrolysis of a substrate (or a composition of matter derived from said culture broth) is permitted to act on such an acetic acid ester, the ester is enantioselectively hydrolyzed to give the desired optically active compound with good efficiency. This invention has been accomplished on the basis of the above finding. As a result, this invention enables production of optically active compounds of value for the synthesis of drugs and agrochemicals with high efficiency.

This invention, therefore, relates to:
(1) A process for producing an optically active form of a compound of the formula (I)

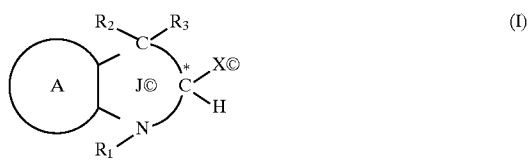

wherein $R_1$ represents hydrogen or a hydrocarbon group that may be substituted; $R_2$ and $R_3$ independently represent hydrogen, a hydrocarbon group that may be substituted, or a heteroaromatic group that may be substituted; X' represents a substituent comprising an esterified carboxyl group or an acylated hydroxyl group; ring A represents a benzene ring that may be substituted or a heteroaromatic ring that may be substituted; ring J' represents a 7- or 8-membered heterocyclic ring containing at most 3 hetero-atoms as ring-constituent members, which may have a further substituent or substituents in addition to $R_1$, $R_2$, $R_3$ and X', and C* denotes a chiral carbon atom or a salt thereof, which comprises subjecting the racemic compound of the formula (I) or a salt thereof to enzymatic enantioselective hydrolysis to provide an optically active form of the compound of the formula (I).

(2) A process of (1) wherein said enzymatic enantioselective hydrolysis is conducted using a culture broth of a microorganism or a preparation derived from said culture broth.

(3) A process of (1) wherein said optically active form of the compound of the formula (I) is isolated.

(4) A process of (1) wherein said compound of the formula (I) is a compound of the formula (II)

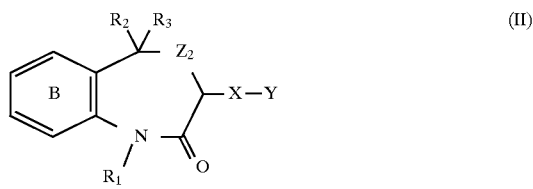

(II)

wherein $R_1$ represents hydrogen or a hydrocarbon group that may be substituted; $R_2$ and $R_3$ independently represent hydrogen, a hydrocarbon group that may be substituted, or a heteroaromatic group that may be substituted; $Z_2$ represents $S(O)_q$ (q denotes 0, 1 or 2) or O; X represents a bond or a divalent atomic chain; Y represents an esterified carboxyl group or an acylated hydroxyl group; ring B represents a benzene ring that may be substituted.

(5) A process of (1) wherein said compound of the formula (I) is a compound of the formula (III)

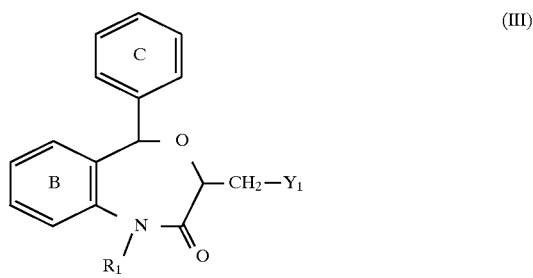

(III)

wherein $R_1$ represents hydrogen or a hydrocarbon group that may be substituted; $Y_1$ represents an esterified carboxyl group; ring B represents a benzene ring that may be substituted and ring C represents a benzene ring that may be substituted.

(6) A process of (2) wherein said microorganism is a strain of bacteria or fungi.

(7) A process of (6) wherein said strain of bacteria is a strain of the genus Pseudomonas or the genus Bacillus.

(8) A process of (7) wherein said strain of the genus Pseudomonas is a strain of *Pseudomonas taetrolens, Pseudomonas diminuta, Pseudomonas aeruginosa* or *Pseudomonas vesicularia*.

(9) A process of (7) wherein said strain of the genus Pseudomonas is a strain selected from among *Pseudomonas taetrolens* IFO 12691, *Pseudomonas diminuta* IFO 13182, *Pseudomonas aeruginosa* IFO 3923, and *Pseudomonas vesicularis* IFO 12165.

(10) A process of (7) wherein said strain of the genus Bacillus is a strain of *Bacillus subtilis*.

(11) A process of (7) wherein said strain of the genus Bacillus is *Bacillus subtilis* IFO 3026.

(12) A process of (6) wherein said strain of fungi is a strain of the genus Humicola or the genus Rhizopus.

(13) A process of (12) wherein said strain of the genus Humicola is a strain of *Humicola lanuginosa*.

(14) A process of (12) wherein said strain of the genus Rhizopus is a strain of *Rhizopus delemer*.

(15) A process for producing an optically active form of a compound of the formula (XII), which comprises subjecting the O-acyl derivative of a racemic compound of the formula (XII):

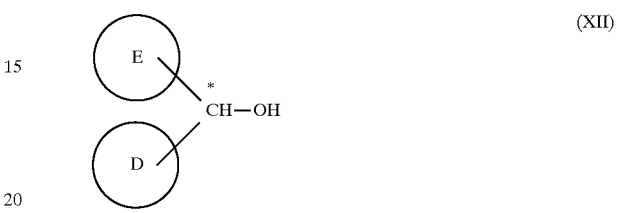

(XII)

wherein ring D represents a benzene ring having an unsubstituted or substituted amino group in the 2-position; ring E represents an unsubstituted or substituted aromatic ring dissimilar to ring D and C* denotes a chiral carbon atom or a salt thereof, to enzymatic enantioselective hydrolysis to provide an optically active form of said compound of the formula (XII) or a salt thereof and the corresponding O-acyl derivative of its antipode.

(16) A process of (15) wherein said optically active form of the compound of the formula (XII) is isolated.

(17) A process of (15) wherein said enzymatic enantioselective hydrolysis reaction is conducted using a culture broth from a microorganism or a preparation derived from said culture broth.

(18) A process of (17) wherein said microorganism is a strain of bacteria, actinomycetes or fungi.

(19) A process of (18) wherein said strain of bacteria is a strain of the genus Pseudomonas or the genus Bacillus.

(20) A process of (18) wherein said strain of actinomycetes is a strain of the genus Streptomyces.

(21) A process of (18) wherein said strain of fungi is a strain of the genus Aspergillus.

(22) A process of (19) wherein said strain of the genus Pseudomonas is a strain selected from among *Pseudomonas sp.S*-6 FERM BP-5205, *Pseudomonas sp.S*-11 FERM BP-5206 and *Pseudomonas sp.S*-13 FERM BP-5207.

(23) A process of (20) wherein said strain of the genus Streptomyces is *Streptomyces sp.*121-39 FERM BP-5208.

(24) A process of (15) wherein said compound of the formula (XII) is a compound of the formula (IV)

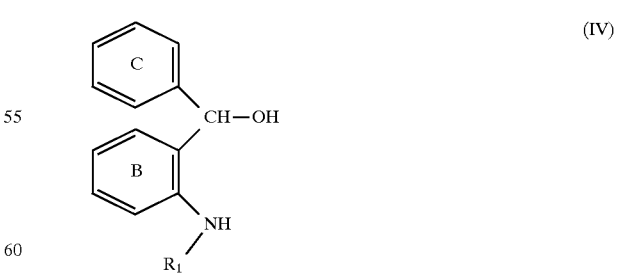

(IV)

wherein $R_1$ represents hydrogen or a hydrocarbon group that may be substituted; ring B represents a benzene ring that may be substituted; and ring C represents a benzene ring that may be substituted, and is dissimilar to ring B.

(25) A process for producing an optically active form of the compound of the formula (III)

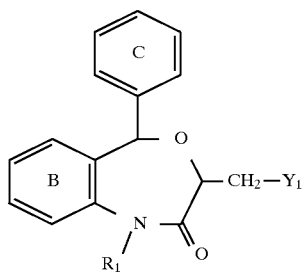

(III)

wherein $R_1$ represents hydrogen or a hydrocarbon group that may be substituted; $Y_1$ represents an esterified carboxyl group; ring B represents a benzene ring that may be substituted; and ring C represents a benzene ring that may be substituted, or a salt thereof which comprises (i) a step of subjecting an O-acyl derivative of a racemic compound of the formula (IV)

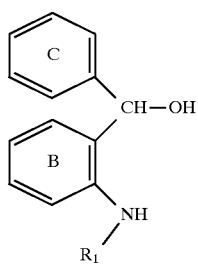

(IV)

wherein the symbols are as defined above, or a salt thereof, to enzymatic enantioselective hydrolysis to provide the optically active form of said compound of the formula (IV) or a salt thereof;

(ii) a step of reacting said optically active form of the compound of the formula (IV) or a salt thereof with a compound of the formula

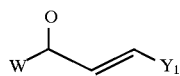

wherein W is a leaving group and $Y_1$ is as defined above and to obtain the optically active form of the compound of the formula (V)

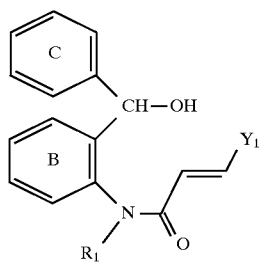

(V)

wherein the symbols are as defined above, or a salt thereof and (iii) a step of subjecting said optically active form of the compound of the formula (V) or a salt thereof to cyclization reaction in the presence of a base to yield the optically active form of the formula (III) or a salt thereof.

(26) An optically active compound of the formula (VI)

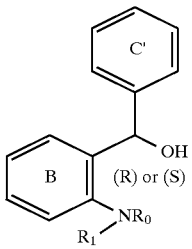

(VI)

wherein $R_0$ is hydrogen or a group of the formula

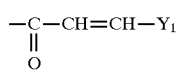

($Y_1$ represents an esterified carboxyl group); $R_1$ is hydrogen or a hydrocarbon group that may be substituted; ring B represents a benzene ring that may be further substituted and ring C' represents a benzene ring having at least a lower alkoxy group and optionally additional substituent(s), dissimilar to ring B.

Referring to the compound of formula (III), the compound which has substituents at 3- and 5-positions in a trans orientation is preferable. Specifically, the preferable optically active form of the compound of formula (III) obtained by the present process can be illustrated by following formula.

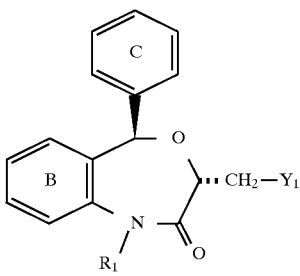

(wherein, each symbol has the same meaning as defined in formula (III)).

The compound of formula (I) is a mixture (racemate or racemic mixture) of a compound of formula (Ia)

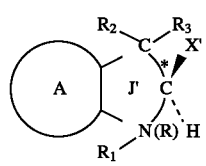

(Ia)

wherein each symbol has the same meaning as defined hereinbefore and a compound of formula (Ib)

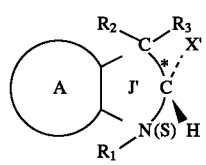

(Ib)

wherein each symbol has the same meaning as defined hereinbefore.

Both the compound of formula (Ia) and the compound of formula (Ib) are optically active compounds and (R) and (S) in the formulas represent R-configuration and S-configuration, respectively.

Referring to the above formulas (I), (II) and (III), the hydrocarbon group of said hydrocarbon group that may be substituted includes aliphatic acyclic hydrocarbon groups, alicyclic hydrocarbon groups, and aryl groups and among them aliphatic acyclic hydrocarbon groups are preferred.

The aliphatic acyclic hydrocarbon group for said hydrocarbon group includes straight-chain or branched aliphatic hydrocarbon groups such as alkyl, alkenyl and alkinyl. Particularly preferred are alkyl groups. The alkyl mentioned just above is preferably a $C_{1-7}$ alkyl group such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, etc., more preferably a $C_{3-5}$ alkyl group such as n-propyl, isopropyl, isobutyl, neopentyl, etc. and, isobutyl and neopentyl are most preferable. The alkenyl mentioned above includes $C_{2-6}$ alkenyl groups such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Preferred, among them, are vinyl, allyl, isopropenyl, 2-methylallyl, 2-methyl-1-propenyl, 2-methyl-2-propenyl and 3-methyl-2-butenyl. The alkinyl also mentioned above includes $C_{2-6}$ alkinyl groups such as ethinyl, 1-propinyl, 2-propinyl, 1-butinyl, 2-butinyl, 3-butinyl, 1-pentinyl, 2-pentinyl, 3-pentinyl, 4-pentinyl, 1-hexinyl, 2-hexinyl, 3-hexinyl, 4-hexinyl, and 5-hexinyl, among others. Particularly preferred are ethinyl, 1-propinyl and 2-propinyl.

The alicyclic hydrocarbon group for said hydrocarbon group includes saturated or unsaturated alicyclic hydrocarbon groups such as cycloalkyl, cycloalkenyl and cycloalkadienyl. The cycloalkyl mentioned just above is preferably a cycloalkyl of 3 to 9 carbon atoms, including but not limited to cyclopropyl, cyclobutyl, cyclopentyl, cyclohexyl, cycloheptyl, cyclooctyl and cyclononyl. Particularly preferred are $C_{3-6}$ cycloakyl groups such as cyclopropyl, cyclobutyl, cyclopentyl and cyclohexyl. The cycloalkenyl mentioned above includes a $C_{3-6}$ cycloalkenyl group such as 2-cyclopenten-1-yl, 3-cyclopenten-1-yl, 2-cyclohexen-1-yl, 3-cyclohexen-1-yl, 1-cyclobuten-1-yl and 1-cyclopenten-1-yl. The cycloalkadienyl mentioned above includes a $C_{3-6}$ cycloalkadienyl group such as 2,4-cyclopentadien-1-yl, 2,4-cyclohexadien-1-yl and 2,5-cyclohexadien-1-yl.

The aryl group for said hydrocarbon group includes $C_{6-16}$ monocyclic or their fused polycyclic aromatic hydrocarbon groups such as phenyl, naphthyl, anthryl, phenanthryl, and acenaphthylenyl. Among others, particularly preferred are $C_{6-10}$ aryl groups such as phenyl, 1-naphthyl and 2-naphthyl.

The substituent for said hydrocarbon group that may be substituted as represented by $R_1$ includes but is not limited to aryl groups that may be substituted, cycloalkyl or cycloalkenyl groups that may be substituted, heterocyclic groups that may be substituted, amino that may be substituted, hydroxyl that may be substituted, thiol that may be substituted, halogen (e.g. fluorine, chlorine, bromine, iodine) and oxo, and this hydrocarbon group may have 1 to 5, preferably 1 to 3, of such substituents in substitutable positions. The aryl group of said aryl that may be substituted includes $C_{6-16}$ aryl groups such as phenyl, naphthyl, anthryl, phenanthryl and acenaphthylenyl, among others. Preferred are $C_{6-10}$ aryl groups such as phenyl, 1-naphthyl, and 2-naphthyl. The substituent for said aryl group that may be substituted includes but is not limited to $C_{1-3}$ alkoxy groups (e.g. methoxy, ethoxy, propoxy, etc.), halogens (e.g. fluorine, chlorine, bromine, iodine), and $C_{1-3}$ alkyl groups (e.g. methyl, ethyl, propyl, etc.), and the aryl group may have 1 to 2 substituents. The cycloalkyl group of said cycloalkyl that may be substituted includes $C_{3-7}$ cycloalkyl groups such as cyclopropyl, cyclobutyl, cyclopentyl, cyclohexyl and cycloheptyl, among others. The kind and number of substituents on said cycloakyl that may be substituted can be the same as those of substituent groups on said aryl that may be substituted. The cycloalkenyl group of said cycloalkenyl that may be substituted includes $C_{3-6}$ cycloalkenyl groups such as cyclopropenyl, cyclobutenyl, cyclopentenyl, and cyclohexenyl, among others. The kind and number of substituents on said cycloalkenyl that may be substituted can be the same as those of substituents on said aryl that may be substituted. The heterocyclic group of said heterocyclic group that may be substituted includes heteroaromatic groups and saturated or unsaturated nonaromatic heterocyclic groups (heteroaliphatic groups), both of which contain at least one (preferably one to four) hetero-atom selected from among oxygen, sulfur and nitrogen as a ring member. Preferred are heteroaromatic groups. Among such heteroaromatic groups are 5 to 6 membered monocyclic heteroaromatic groups (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.) and condensed heteroaromatic groups which contain 2 to 3 rings selected from 5 to 8 membered rings (e.g. benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo(4,3-b]pyridazinyl, among others. Preferred are 5 to 6 membered monocyclic heteroaromatic groups containing one or two hetero-atom as a ring nember such as furyl, thienyl, indolyl, isoindolyl, pyrazinyl, pyridyl and pyrimidinyl. The non-aromatic heterocyclic group mentioned above includes 4 to 8 membered nonaromatic heterocyclic groups such as oxiranyl, azetidinyl, oxetanyl, thietanyl, pyrrolidinyl, tetrahydryl, thiolanyl, piperidyl, tetrahydropyranyl, morpholinyl, thiomorpholinyl and piperazinyl. Said heterocyclic group that may be substituted may contain 1 to 4, preferably 1 to 2 substituents which include $C_{1-3}$ alkyl groups (e.g. methyl, ethyl, propyl, etc.). The substituent for said amino that may be substituted, for said hydroxyl that may be substituted, or for said thiol that may be substituted includes lower($C_{1-3}$) alkyl groups (e.g methyl, ethyl, propyl, etc.). Where the hydrocarbon group of said hydrocarbon group that may be substituted, as represented by $R_1$, is an alicyclic hydrocarbon group or an aryl group, $C_{1-3}$ alkyl groups (e.g. methyl, ethyl, propyl, etc.) can be mentioned as further examples of its substituent.

The example of said $R_1$ that may be substituted by oxo include acyl group obtained by removing the OH group from a carboxylic acid.

Further examples of $R_1$ are optionally substituted $C_{1-6}$ acyl groups (e.g. formyl, acetyl, propionyl, butyryl, isobutyryl, valeryl, isovaleryl, pivaloyl, hexanoyl, dimethylacetyl, trimethylacetyl, etc.). The acyl group for $R_1$ may have 1 to 5 substituents in substitutable positions, and halogen (e.g. fluorine, chlorine, bromine) may be mentioned as an example of such substituent group.

Referring to formulas (I) and (II), the hydrocarbon group of said hydrocarbon group that may be substituted, as represented by $R_2$ and $R_3$, includes aliphatic acyclic hydrocarbon groups, alicyclic hydrocarbon groups, and aryl groups. Preferred are aliphatic acyclic hydrocarbon groups and aryl groups.

The aliphatic acyclic hydrocarbon group for said hydrocarbon group includes straight-chain or branched aliphatic hydrocarbon groups such as alkyl, alkenyl and alkinyl groups. Preferred are alkyl groups. The alkyl group includes $C_{1-6}$ alkyl groups such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and 2-ethylbutyl, among others. Preferred are $C_{1-4}$ alkyl groups such as methyl, ethyl, propyl, isopropyl, isobutyl, butyl and t-butyl, among others. The alkenyl mentioned above includes $C_{2-6}$ alkenyl groups such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl, among others. Preferred are vinyl, allyl, isopropenyl, 2-methylallyl, 2-methyl-1-propenyl, 2-methyl-2-propenyl, and 3-methyl-2-butenyl. The alkinyl mentioned above includes $C_{2-6}$ alkinyl groups such as ethinyl, 1-propinyl, 2-propinyl, 1-butinyl, 2-butinyl, 3-butinyl, 1-pentinyl, 2-pentinyl, 3-pentinyl, 4-pentinyl, 1-hexinyl, 2-hexinyl, 3-hexinyl, 4-hexinyl, and 5-hexinyl, among others. Preferred are ethinyl, 1-propinyl and 2-propinyl.

The alicyclic hydrocarbon group for said hydrocarbon group includes the groups mentioned previously for the alicyclic hydrocarbon group $R_1$.

The aryl group for said hydrocarbon group includes $C_{6-16}$ aryl groups such as monocyclic and fused polycyclic aromatic hydrocarbon groups, such as phenyl, naphthyl, anthryl, phenanthryl and acenaphthylenyl, among others. Preferred are $C_{6-10}$ aryl groups such as phenyl, 1-naphthyl and 2-naphthyl.

The substituent for said "hydrocarbon group that may be substituted" for $R_2$ and $R_3$ includes the groups specifically mentioned as the substituent on said "hydrocarbon group that may be substituted" for $R_1$. One to four (preferably one to two) such substituents may present at any possible position of said hydrocarbon group.

Where $R_2$ and $R_3$ independently represent "an alkyl group that may be substituted", the substituent on such alkyl includes halogen (e.g. fluorine, chlorine, bromine, iodine) and lower ($C_{1-4}$)alkoxy (e.g. methoxy, ethoxy, propoxy, isopropoxy, butoxy, t-butoxy, etc.), to mention but a few preferred species.

Where $R_2$ and $R_3$ independently represent "an aryl group that may be substituted", the substituent on such aryl includes halogen (e.g. fluorine, chlorine, bromine, iodine), lower alkyl that may be substituted, lower alkoxy that may be substituted, hydroxyl that may be substituted, nitro and cyano, to mention some preferred examples. These substituents, identical or different, may be present in 1 to 3 (preferably 1 to 2) positions. The lower alkyl mentioned just above includes $C_{1-4}$ alkyl groups such as methyl, ethyl, n-propyl, isopropyl, n-butyl, isobutyl, sec-butyl, and tert-butyl, among others. Preferred are methyl and ethyl. The lower alkoxy mentioned above includes $C_{1-4}$ alkoxy groups such as methoxy, ethoxy, n-propoxy, isopropoxy, n-butoxy, isobutoxy, sec-butoxy, and tert-butoxy, among others. Preferred are methoxy and ethoxy. The substituent on said lower alkyl or lower alkoxy that may be substituted includes halogen (e.g. fluorine, chlorine, bromine, iodine) and may be present at 1 to 5 positions. The substituent on said hydroxyl that may be substituted includes lower($C_{1-4}$)alkyl (e.g. methyl, ethyl, propyl, isopropyl, butyl, t-butyl, etc.), $C_{3-6}$ cycloalkyl (e.g. cyclopropyl, cyclobutyl, cyclopentyl, cyclohexyl, etc.), $C_{6-16}$ aryl (e.g. phenyl, 1-naphthyl, 2-naphthyl, etc.), and $C_{7-14}$ aralkyl (e.g. benzyl, phenethyl, etc.), among others. These substituents may form a ring structure with adjacent substituent, and for example, where said aryl group that may be substituent represented by $R_2$ or $R_3$ is phenyl, the following structures may be formed.

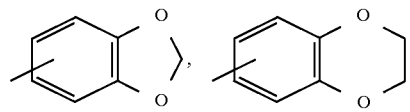

Each of such ring structures may be further substituted by one to four, for example, lower($C_{1-3}$)alkyl (e.g. methyl, ethyl, propyl, isopropyl, etc.).

The heteroaromatic group of said "heteroaromatic group that may be substituted" for $R_2$ and $R_3$ includes the heteroaromatic groups mentioned specifically for the substituent in $R_1$. Preferred are 5 to 6 membered monocyclic heteroaromatic groups such as furyl, thienyl, indolyl, isoindolyl, pyrazinyl, pyridyl, pyrimidyl and imidazolyl. Such heteroaromatic group may have one to four substituent(s). The substituent on such heteroaromatic group may for example be $C_{1-3}$ alkyl (e.g. methyl, ethyl, propyl, etc.).

Either $R_2$ or $R_3$ is preferably a hydrogen atom.

Among the groups mentioned above for $R_2$ and $R_3$, phenyl that may be substituted is preferred. Particularly for one of $R_2$ and $R_3$, preferred is phenyl substituted by halogen (e.g. chlorine, bromine) and/or lower $C_{1-3}$ alkoxy, and the other of $R_2$ and $R_3$ is preferably a hydrogen atom.

Referring to formula (I), said "substituent group comprising an esterified carboxyl group" for X' includes substituents each having an esterified carboxyl group as well as esterified carboxyl groups. The esterified carboxyl group may be the same as the esterified carboxyl group defined below for Y.

The substituent group comprising an acylated hydroxyl group for X' includes substituent groups having an acylated hydroxyl group and acylated hydroxyl groups. The acylated hydroxyl group may be the same as the acylated hydroxyl group defined below for Y.

X' may for example be a group of formula (a)

wherein X represents a bond or a divalent atomic chain; Y represents an esterified carboxyl group or an acylated hydroxyl group.

In formula (a), the "divalent atomic chain" for X may be any divalent chain preferably comprising a linear portion composed of 1 to 7 atoms, preferably 1 to 4 atoms, and may have a side chain. Particularly, X is a divalent atomic chain containing 1 to 2 atom(s) in terms of the efficiency of enzymatic enantioselective hydrolysis according to the present invention.

For example, X may represent the following formula.

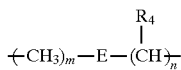

In the above formula, m and n independently represent 0, 1, 2 or 3 and E represents a bond, oxygen, sulfur, sulfoxide, sulfone, —N($R_5$)—, —NHCO—, —CON($R_6$)—, or —NHCONH—, where $R_4$ and $R_6$ each represents hydrogen, lower alkyl that may be substituted, aralkyl that may be substituted, or phenyl that may be substituted. $R^5$ represents hydrogen, lower alkyl, aralkyl or acyl.

The alkyl group of said "lower alkyl that may be substituted" for $R_4$ and $R_6$ includes straight-chain or branched lower($C_{1-6}$)alkyl groups (e.g. methyl, ethyl, n-propyl, isopropyl, n-butyl, isobutyl, tert-butyl, n-pentyl, isopentyl, neopentyl, etc.). Said lower alkyl that may be substituted may contain one to four (preferably one to two) substituents. The substituent on said lower alkyl that may be substituted includes 5- to 6-membered heteroaromatic groups containing 1 to 4 hetero atoms selected from atoms of oxygen, nitrogen and sulfur (e.g. furyl, thienyl, indolyl, isoindolyl, pyrazinyl, pyridyl, pyrimidyl, imidazolyl, etc.), amino (e.g. amino, mono or di substituted amino) that may be substituted, hydroxyl that may be substituted, thiol that may be substituted, carboxyl that may be esterified, and halogen (e.g. fluorine, chlorine, bromine, iodine), among others. The substituent for said amino that may be substituted, for said hydroxyl that may be substituted, or for said thiol that may be substituted includes lower ($C_{1-3}$)alkyl groups (e.g. methyl, ethyl, propyl, etc.). The carboxyl that may be esterified includes $C_{2-5}$ alkoxycarbonyl and $C_{7-11}$ aryloxycarbonyl groups such methoxycarbonyl, ethoxycarbonyl, propoxycarbonyl, phenoxycarbonyl, and 1-naphthoxycarbonyl. Preferred are methoxycarbonyl, ethoxycarbonyl and propoxycarbonyl.

The aralkyl group of said "aralkyl that may be substituted" for $R_4$ and $R_6$ includes a $C_{7-15}$ aralkyl group such as includes benzyl, naphthylmethyl, phenylpropyl and phenylbutyl, among others. The aralkyl group may have one to 4, preferably one to 2 substituent(s). The substituent for said aralkyl that may be substituted includes for example, halogen (e.g. fluorine, chlorine, bromine, iodine), $C_{1-3}$ alkoxy (e.g. methoxy, ethoxy, propoxy, etc.), hydroxyl, amino, carboxyl and sulfhydryl.

The substituent for said "phenyl that may be substituted" for $R_4$ and $R_6$ includes halogen (e.g. fluorine, chlorine, bromine, iodine), $C_{1-3}$ alkoxy (e.g. methoxy, ethoxy, propoxy, etc.), and $C_{1-3}$ alkyl (e.g. methyl, ethyl, propyl, etc.), among others.

It should be understood that $R_4$ may vary with different methylene units.

The "lower alkyl" and "aralkyl" for $R_5$ include lower ($C_{1-4}$)alkyl (e.g. methyl, ethyl, propyl, butyl, tert-butyl, etc.) and $C_{7-15}$ aralkyl (e.g. benzyl, phenethyl, phenylpropyl, phenylbutyl, naphthylmethyl, etc.), respectively.

The "acyl" for $R_5$ includes lower $C_{1-6}$ alkanoyl (e.g. formyl, acetyl, propionyl, butyryl, isobutyryl, valeryl, isovaleryl, pivaloyl, hexanoyl, etc.), lower $C_{3-7}$ alkenoyl (e.g. acryloyl, methacryloyl, crotonoyl, isocrotonoyl, etc.), $C_{4-7}$ cycloalkanecarbonyl (e.g. cyclopropanecarbonyl, cyclobutanecarbonyl, cyclopentanecarbonyl, cyclohexanecarbonyl, etc.), lower $C_{1-4}$ alkanesulfonyl (e.g. mesyl, ethanesulfonyl, propanesulfonyl, etc.), aroyl (e.g. benzoyl, p-toluoyl, 1-naphthoyl, 2-naphthoyl, etc.), $C_{6-10}$ aryl(lower)$C_{1-4}$ alkanoyl (e.g. phenylacetyl, phenylpropionyl, hydroatropoyl, phenylbutyryl, etc.), $C_{6-10}$ aryl(lower)$C_{3-5}$ alkenoyl (e.g. cinnamoyl, atropoyl, etc.), and $C_{6-10}$ arenesulfonyl (e.g. benzenesulfonyl, p-toluenesulfonyl, etc.), among others.

X may further be a carbon chain containing a double bond or —L—CH(OH)— (where L represents a bond or a straight-chain or branched alkylene chain). The "carbon chain containing a double bond" is preferably one comprising a linear portion composed of 2–7 atoms, more preferably 2–4 atoms, and may have a side chain. The double bond in this carbon chain may be present in either one or both of the linear and branch portions but is preferably present in the linear portion. The number of double bonds in the carbon chain is not restricted but is preferably one or two.

The carbon chain containing at least one double bond includes but is not limited to 2–7 alkenylene such as vinylene, propenylene, butenylene, butadienylene, methylpropenylene, ethylpropenylene, propylpropenylene, methylbutenylene, ethylbutenylene, propylbutenylene, methylbutadienylene, ethylbutadienylene, propylbutadienylene, pentenylene, hexenylene, heptenylene, pentadienylene, hexadienylene, and heptadienylene. Preferred are vinylene, propenylene, butenylene and butadienylene.

The "straight-chain or branched alkylene chain" for L includes but is not limited to straight-chain or branched $C_{1-6}$ alkylene chains such as methylene, ethylene, trimethylene, tetramethylene, pentamethylene, hexamethylene, heptamethylene, propylene, ethylmethylene, ethylethylene, propylethylene, butylethylene, methyltetramethylene, and methyltrimethylene, among others. Preferred are $C_{1-3}$ alkylene groups such as methylene, ethylene, trimethylene and propylene.

Preferred, among the above species of X', is a group of formula (b) wherein $Y_1$ represents an esterified carboxyl group; X has the same meaning as defined hereinbefore.

Referring to formulas (a) and (b), the "divalent atomic chain" for X is preferably a straight-chain or branched alkylene chain comprising a linear portion composed of 1–4 (preferably 1) carbon atoms. The alkylene chain mentioned above includes such divalent groups as methylene, ethylene, trimethylene, tetramethylene, pentamethylene, hexamethylene, heptamethyiene, propylene, ethylmethylene, ethylethylene, propylethylene, butylethylene, methyltetramethylene, and methyltrimethylene, among others. Preferred are $C_{1-4}$ alkylene groups such as methylene, ethylene, trimethylene and propylene.

Referring, further, to formulas (a) and (b), the "esterified carboxyl group" for Y and $Y_1$ includes $C_{2-7}$ alkoxycarbonyl (e.g. lower($C_{1-6}$)alkoxycarbonyl groups such as methoxycarbonyl, ethoxycarbonyl, propoxycarbonyl, isopropoxycarbonyl, butoxycarbonyl, isobutoxycarbonyl, tert-butoxycarbonyl, sec-butoxycarbonyl, pentyloxycarbonyl, isopentyloxycarbonyl, sec-pentyloxycarbonyl, neopentyloxycarbonyl, tert-pentyloxycarbonyl, etc.), and $C_{7-14}$ aryloxycarbonyl (e.g. phenoxycarbonyl, 1-naphtoxycarbonyl), $C_{8-12}$ aralkyloxycarbonyl (e.g. benzyloxycarbonyl, etc.). Preferred are lower alkoxycarbonyl (e.g. methoxycarbonyl, ethoxycarbonyl, etc.), phenoxycarbonyl, and benzyloxycarbonyl.

The "acylated hydroxyl group" for Y includes hydroxyl substituted by any of $C_{1-6}$ acyl groups (e.g. formyl, acetyl, propionyl, butyryl, isobutyryl, valeryl, isovaleryl, pivaloyl, hexanoyl, dimethylacetyl, trimethylacetyl, etc.). These acyl groups may each have 1–5 substituents in substitutable positions, and halogen (e.g. fluorine, chlorine, bromine) atoms can be mentioned as such substituents.

Among the species mentioned above for X', alkyl groups particularly, $C_{1-3}$ alkyl groups substituted by an esterified carboxyl group are preferred.

In formula (I), the heteroaromatic group represented by ring A includes the heteroaromatic groups mentioned specifically for the substituent in $R_1$. Particularly preferred are the following heteroaromatic groups.

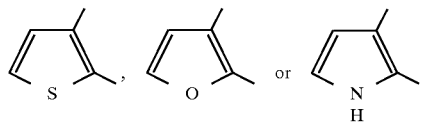

The substituent in ring A for said "benzene ring that may be substituted" and "heteroaromatic ring that may be substituted includes halogen (e.g. fluorine, chlorine, bromine, iodine), lower($C_{1-4}$)alkyl (e.g. methyl, ethyl, propyl, butyl, tert-butyl, etc.) that may be substituted, lower($C_{1-4}$)alkoxy (e.g. methoxy, ethoxy, propoxy, isopropoxy, butoxy, tert-butoxy, etc.) that may be subsituted, hydroxyl, nitro, and cyano, among others. Ring A may have 1–3 and preferably 1–2 such substituent groups. These substituent groups, when located adjacent to each other, may form a ring system. The substituent for said lower $C_{1-4}$ alkyl that may be substituted or for said lower $C_{1-4}$ alkoxy that may be substituted includes halogen (e.g. fluorine, chlorine, bromine, iodine) and may be present in 1–3 positions. Ring A is preferably one substituted by methoxy or chlorine, and preferably by chlorine.

Referring to the formulas (II) and (III), the substituent for said "benzene ring that may be substituted" for ring B includes but is not limited to halogen (e.g. fluorine, chlorine, bromine, iodine), lower($C_{1-4}$)alkyl (e.g. methyl, ethyl, propyl, butyl, tert-butyl, etc.) that may be substituted, lower: ($C_{1-4}$)alkoxy (e.g. methoxy, ethoxy, propoxy, isopropoxy, butoxy, tert-butoxy, etc.) that may be substituted, hydroxyl, nitro, and cyano. Ring B may have 1–3, preferably 1 or 2, of such substituents. These substituents, if adjacent to each other, may form a ring therebetween. The substituent for said lower alkyl that may be substituted or for said lower alkoxy that may be substituted includes halogen (e.g. fluorine, chlorine, bromine, iodine) and may be present in 1–3 positions. Ring B is preferably one substituted by methoxy or chlorine and, preferably by chlorine.

Referring to formula (I), the 7- or 8-membered heterocycle containing at most 3 hetero-atoms as ring-constituent memberes" for ring J' includes saturated or unsaturated (preferably saturated) 7- or 8-membered heterocyclic group containing at least one of O, $S(O)_q$ (q is equal to 0, 1 or 2) and N. However, the total number of hetero-atoms as ring members is not more than 3 (preferably 2).

In addition to the groups represented by $R_1$, $R_2$, $R_3$ and X', ring J' may further have 1–2 substituent groups in substitutable positions. This substituent, where attached to a nitrogen atom of ring J', includes alkyl (e.g. $C_{1-6}$ alkyl groups such as methyl, ethyl, n-propyl, isopropyl, n-butyl, isobutyl, tert-butyl, n-pentyl, isopentyl, neopentyl, etc.) and acyl (e.g. $C_{1-4}$ acyl groups such as formyl, acetyl, propionyl, butyroyl, etc.). These alkyl and acyl groups may in turn be substituted by 1 to 5 halogen atoms (e.g. fluorine, chlorine, bromine, iodine). The substituent, where attached to a carbon atom of ring J', includes but is not limited to oxo, thioxo, hydroxyl that may be substituted (e.g. OH, methoxy, ethoxy, propoxy, iso-propoxy, propenyloxy, allyloxy, butoxy, isobutoxy, sec-butoxy, t-butoxy, 2-butenyloxy, 3-butenyloxy, iso-butenyloxy, pentoxy, isopentoxy, hexyloxy, etc.) and amino that may be substituted (e.g. amino, methylamino, ethylamino, propylamino, propenylamino, isopropylamino, allylamino, butylamino, isobutylamino, dimethylamino, methylethylamino, etc.).

Preferably, ring J' is substituted by oxo or thioxo in addition to the groups $R_1$, $R_2$, $R_3$ and X'.

The fused ring structrue consisting of ring A and ring J' includes but is not limited to:

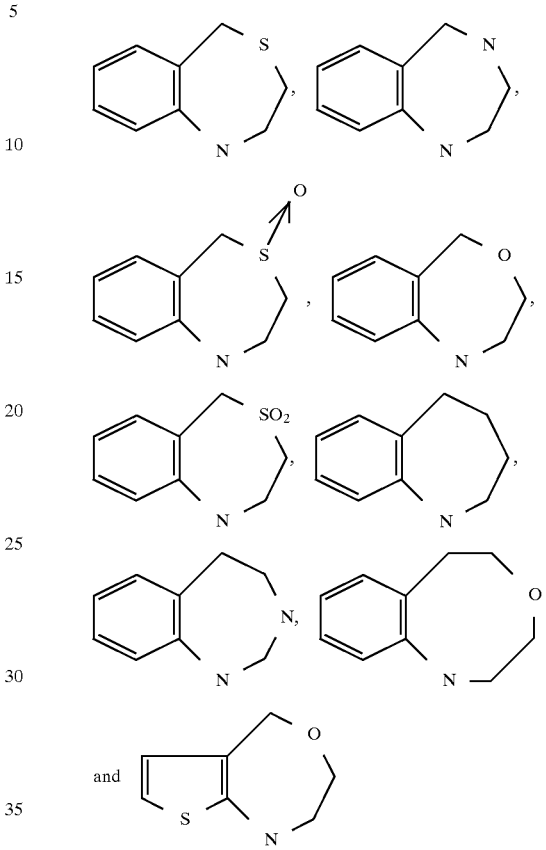

Preferred species of the compound of formula (I) are those of formula (IA).

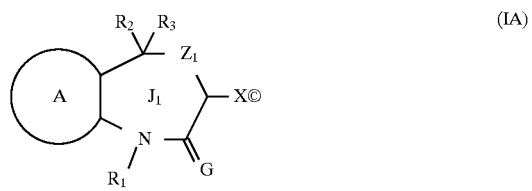

wherein $R_1$, $R_2$, $R_3$, X', and ring A are as defined hereinbefore; ring $J_1$, represents a 7-membered heterocycle; $Z_1$ represents —$N(R_7)$— (where $R_7$ is hydrogen, alkyl or acyl), —$S(O)_q$— (q is equal to 0, 1 or 2), —$CH_2$—, or —O—; G represents O or S).

In the above formula (IA), the alkyl for $R_7$ includes straight-chain or branched lower($C_{1-6}$)alkyl groups (e.g. methyl, ethyl, n-propyl, isopropyl, n-butyl, isobutyl, tert-butyl, n-pentyl, isopentyl, neopentyl, etc.) which may be substituted by 1–5 substituent groups such as halogen (e.g. fluorine, chlorine, bromine, iodine).

The acyl for $R_7$ includes $C_{1-4}$ acyl groups (e.g. formyl, acetyl, propionyl, butyryl, etc.) which may have 1–5 substituent groups, such as halogen (e.g. fluorine, chlorine, bromine, iodine).

In formula (IA), $Z_1$ is preferably $S(O)_q$ (q is equal to 0, 1 or 2) or O. G is preferably O.

Among compounds of formula (IA), those represented by formula (II) are preferred.

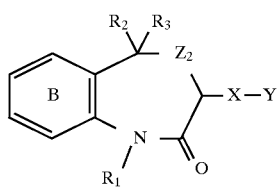

(II)

wherein each symbol has the meaning defined hereinbefore.

Particularly preferred, among compounds of formula (II), are those of formula (III).

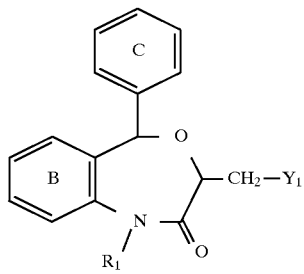

(III)

wherein each symbol has the meaning defined hereinbefore.

The compounds of the formulas (I), (IA), (II) and (III) can be respectively prepared by known processes, such as those disclosed in EP Laid-open No. 567026 and JP Application Laid-open No. 15531/1994, JP Applications 229159/1994, and 229160/1994, among other patent literature.

These compounds have squalene synthase inhibitory activity, cholesterol-lowering activity and triglyceride concentration-lowering activity. They are of value in prevent and treatment of hypercholesterolemia and can be used according to the description cited in the above patent literature.

The process according to this invention can be exploited with great advantage for the production of optically active forms of compounds having plasma cholesterol and triglyceride concentration lowering activities as disclosed in EP Laid-open No. 567026, JP Application Laid-open No. 15531/1994, EPA645377 (based on JP Application No. 229159/1994) and EPA 645378 (based on JP Application 229160/1994), among other literature.

Referring to formula (III), the substituent for said "benzene ring that may be substituted" for ring C includes but is not limited to halogen (e.g. fluorine, chlorine, bromine, iodine), lower alkyl that may be substituted, lower alkoxy that may be substituted, hydroxyl that may be substituted, nitro and cyano. These substituent groups, which may be similar or dissimilar, may be present in 1–3 (preferably 1 or 2) positions. The lower alkyl mentioned just above includes $C_{1-4}$ alkyl such as methyl, ethyl, n-propyl, isopropyl, n-butyl, isobutyl, sec-butyl, and tert-butyl, among others. Preferred are methyl and ethyl. The lower alkoxy mentioned above includes $C_{1-4}$ alkoxy such as methoxy, ethoxy, n-propoxy, isopropoxy, n-butoxy, isobutoxy, sec-butoxy, and tert-butoxy, among others. Preferred are methoxy and ethoxy. The substituent for said lower alkyl or lower alkoxy includes halogen (e.g. fluorine, chlorine, bromine, iodine) and may be present in 1–5 positions. The substituent for said hydroxyl that may be substituted includes lower($C_{1-4}$)alkyl (e.g. methyl, ethyl, propyl, isopropyl, butyl, t-butyl, etc.), $C_{3-6}$ cycloalkyl (e.g. cyclopropyl, cyclobutyl, cyclopentyl, cyclohexyl, etc.), $C_{6-10}$ aryl (e.g. phenyl, 1-naphthyl, 2-naphthyl, etc.), and $C_{7-14}$ aralkyl (e.g. benzyl, phenethyl, etc.).

The salts of the compounds represented by the formulas (I), (Ia), (Ib), (II) and (III) include pharmacologically acceptable salts, for example salts with inorganic acids such as hydrochloric acid, hydrobromic acid, sulfuric acid, phosphoric acid, etc., salts with organic acids such as acetic-acid, tartaric acid, citric acid, fumaric acid, maleic acid, toluenesulfonic acid, methanesulfonic acid, etc., salts with metals such as sodium, potassium, calcium, aluminum, etc., and salts with bases such as triethylamine, guanidine, ammonium, hydrazine, quinine and cinchonine, among others. Particularly, sodium salts are preferred.

In accordance with this invention, a mixture of dextrorotatory and levorotatory forms of a compound of the formula (I) is contacted with a culture broth from a microorganism capable of catalysing enantioselective hydrolysis (or a composition of matter derived therefrom) to obtain an optically active form of said compound.

By way of specific illustration, a mixture of a compound of formula (Ia) and a compound of formula (Ib) is allowed to contact a culture broth from a microorganism capable of catalysing enantioselective hydrolysis or a composition of matter derived therefrom to provide one of said compounds.

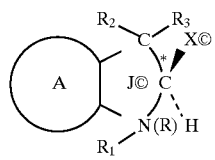

(Ia)

wherein each symbol has the meaning defined hereinbefore

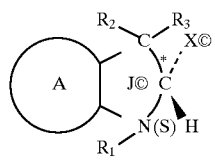

(Ib)

wherein each symbol has the meaning defined hereinbefore

As a result, either the compound of formula (Ia) is specifically converted to a compound of formula (Iah)

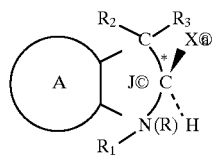

(Iah)

wherein X'a represents a substituent group comprising a carboxyl or hydroxyl group; the other symbols are as defined hereinbefore or the compound of formula (Ib) is specifically converted to the compound of formula (Ibh).

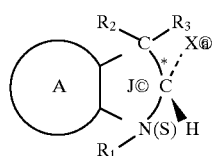

(Ibh)

wherein X'a represents a substituent group comprising a carboxyl or hydroxyl group; the other symbols are as defined hereinbefor The derived optically active compound can be isolated by purifying the above reaction mixture by per se known procedures such as distillation, recrystallization, solvent extraction, redistribution, crystallization, and chromatography (e.g. column chromatography), among other procedures.

In this connection, when the derived compound is a compound of the formula (Iah), a culture broth from a microorganism capable of catalysing enantioselective hydrolysis of the compound (Ia) or a composition of matter derived from said culture broth is employed. An alternative process is as follows.

First, using a culture broth from a microorganisms capable of causing chiral hydrolysis of the compound of formula (Ib) or a composition of matter derived therefrom, a mixture of the compound of formula (Ibh) (chiral hydrolysate) and the compound of formula (Ia) is obtained. Then, the compound of formula (Ia) is isolated from said mixture and hydrolyzed, chemically or enzymatically, to the compound of formula (Iah).

The strain of microorganism for use in accordance with this invention may be any strain of microorganism that is able to cause chiral hydrolysis of a compound of the formula (I) and includes strains belonging to the taxonomic categories of bacteria and fungi (ray fungi and molds). As said bacteria, those of the genera Pseudomonas and Bacillus can be mentioned by way of example. The species of the genus Pseudomonas includes *Pseudomonas taetrolens, P. diminuta, P. aeruginosa,* and *E. vesicularis,* among others. Typically, *Pseudomonas taetrolens* IFO 12691, *Pseudomonas diminuta* IFO 13182, *Pseudomonas aeruginosa* IFO 3923 and *Pseudomonas vesicularis* IFO 12165 can be mentioned. The species of the genus Bacillus includes *Bacillus subtilis* and typically *B. subtilis* IFO 3026. The type culture strains to which IFO numbers are assigned as above are listed in List of Cultures, 9th Ed., 1992 (Institute for Fermentation (Yodogawa-ku, Osaka) and are available from the Institute. The fungi that can be employed may for example be filamentous fungi belonging to the genus Humicola or the genus Rhizopus. As a species of Humicola, *Humicola lanuginosa* can be mentioned. As a species of Rhizopus, *Rhizopus delemer* can be mentioned. Further, lipases purified from cultures of *Humicola lanuginosa* and *Rhizopus delemer,* respectively, are commercially available from Cosmo Bio Co., Ltd. as products of Biocatalyst Ltd., England [General Catalog No. 9, 1993–95). While the above-mentioned microorganisms can be used as they are, those subjected to mutagenic treatment for enhanced substrate conversion and stereospecificity of the reaction can be employed.

The medium for the cultivation of said microorganism is not critical but can be of any kind that enables growth of the microorganism. By permitting a culture broth from the microorganism or a composition of matter derived therefrom to act on the compound of the formula (I), the desired optically active compound can be provided.

The carbon source that can be used in the culture medium includes but is not limited to glucose, sucrose, maltose, dextrin, starch, glycerol, oils and fats (e.g. soybean oil, olive oil, etc.), and a variety of fatty acids (e.g. palmitic acid, stearic acid, oleic acid, etc.). The nitrogen source that can be used includes but is not limited to meat extract, yeast extract, peptone, dried yeast, soybean flour, defatted soybean meal, corn steep liquor, peptone, casein, cottonseed flour, urea, and various ammonium salts (e.g. ammonium sulfate, ammonium chloride, ammonium nitrate, ammonium acetate, etc.). The inorganic salt that can be used includes potassium dihydrogen phosphate, potassium monohydrogen phosphate, sodium dihydrogen phosphate, sodium monohydrogen phosphate, sodium nitrate, magnesium sulfate, calcium carbonate, sodium chloride, other salts of Na, K, Ca and Mg, and salts of iron, manganese, zinc, cobalt and nickel, among other salts. In addition to the above medium components, such other substances as amino acids, peptides, vitamins, and nucleic acid compounds can also be incorporated. Inorganic and/or organic acids can be added for the purpose of controlling the pH of the medium, and oils or surfactants can be used in appropriate amounts for defoaming purposes. The pH of the medium may range from 5 to 9 and is preferably 6 to 8.

Cultivation is carried out by whichever of the stationary cultural method and the aerobic agitation method. The incubation temperature is about 20°–45° C. and preferably about 28°–37° C. The incubation time is about 10–96 hours and preferably about 16–72 hours.

The "culture broth" used in this method is a fermentation broth obtained by cultivation of any of said microorganisms. The "composition of matter derived from the culture broth" means any of the cells havested by filtering or centrifuging the culture broth, the filtrate or supernatant similarly obtained, the disrupted cells or cell extract obtainable by sonication, French press processing, alumina ball milling, or treatment with a lytic enzyme, a surfactant, or an organic solvent, and the enzyme preparation purified from said culture filtrate or supernatant or said cell extract by, for example, ammonium sulfate precipitation, ion exchange chromatography, adsorption chromatography, gel permeation chromatography or affinity chromatography. The cells or enzyme immobilized on a celite or other support can likewise be employed.

In accordance with this invention, said optically active substance can be obtained by mixing the substrate compound of the formula (I) with the culture broth obtained by growing any of said microorganisms or said composition of matter derived therefrom. Where the culture broth is employed, the reaction can be carried out by adding the substrate to the culture broth. In this procedure, the substrate can be added to the medium concurrently with inoculation, prior to inoculation, or during the growth phase of the microorganism. The substrate may be directly added to the reaction system or added after dissolution in an organic solvent (e.g. N,N-dimethylformamide, N,N-dimethylacetamide, dimethyl sulfoxide, ethanol, methanol, toluene, etc.) at a suitable concentration.

Where an enzyme purified from the culture broth is used for the reaction, the enzyme may be dissolved in a suitable solvent (e.g. aqueous sodium chloride solution, phosphate buffer, tris-HCl buffer, etc.) and the solution be submitted to the reaction. In this procedure, too, the substrate may be dissolved in a suitable solvent beforehand. As an alternative procedure, the enzyme may be added to a solution of the substrate in a suitable solvent. In this case, too, the enzyme may be previously dissolved in a suitable solvent. It is also possible to dissolve both the enzyme and the substrate concurrently in a common solvent.

While this reaction can be carried out in aqueous medium, it can be conducted in an organic solvent (e.g. toluene, ethyl acetate, isopropyl ether, dichloromethane, etc.) or in a binary system composed of water and an organic solvent.

For the purposes of this reaction, the concentration of the starting compound (substrate) in the reaction system is about 0.1–100 mg/ml, preferably about 5–30 mg/ml and most preferably about 1–10 mg/ml. The amount of the culture broth or the composition of matter derived therefrom in terms of the equivalent wet weight of cells is 1–50 mg per ml of the reaction system. The reaction temperature is about 15°–80° C. and preferably about 20°–42° C. The pH is about 4–11 and preferably about 6–9. The reaction time is about 10 minutes to 96 hours and preferably about 1–48 hours. Where necessary or desired, an organic solvent, a reaction accelerator, an enzyme stabilizer, etc. can be added to the reaction system. The reaction can be conducted under stationary condition, shaking or agitation. Where necessary, it is possible to immobilize the cells or enzyme on a suitable support and conduct the reaction in a bioreactor.

In the reaction according to this invention, the rate of conversion from the compound of the formula (I) to the compound of formula (Ih)

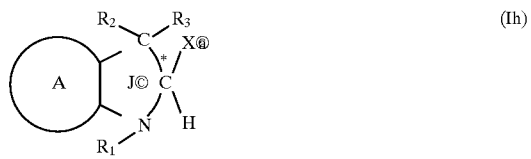

wherein X'a represents a substituent group comprising a carboxyl or hydroxyl group; the other symbols have the same meaning as defined hereinbefore can be calculated by means of the following equation.

$$\text{Conversion } (\%) = \frac{\text{Compound(Iah)} + \text{compound(Ibh)}}{\text{Compound(Ia)} + \text{compound(Ib)} + \text{compound(Iah)} + \text{compound(Ibh)}} \times 100$$

where compound (Ia), compound (Ib), compound (Iah), and compound (Ibh) represent the amounts of the respective compounds after reaction The optical purity of the product (or the substrate), taking the production of compound (Iah) as an example, can be calculated by means of the following equation.

$$\text{Optical purity } (\% \, ee) \frac{\text{Compound(Iah)} - \text{compound(Ibh)}}{\text{Compound(Iah)} + \text{compound(Ibh)}} \times 100$$

where compound (Iah) and compound (Ibh) represent the same meanings as defined above.

The amounts after reaction of said compound (Ia), compound (Ib), compound (Iah) and compound (Ibh) can be determined by, for example, the following method.

The reaction system after completion of the reaction is made acidic with acetic acid or the like, a suitable amount (e.g. one volume) of an organic solvent (e.g. ethyl acetate) is then added, and the mixture is stirred. The organic layer is subjected to high performance liquid chromatography (HPLC) using a suitable chiral column (e.g. Ultron ES-OVM). In this manner, the amounts of compounds (Ia), (Ib), (Iah) and (Ibh) can be respectively determined.

The following description relates to the production of optically active form of a compound represented by formula (XII). Basically, an O-acyl derivative of a racemic compound of formula (XII) [hereinafter sometimes referred to as the O-acyl derivative of the racemic compound] is subjected to enzymatic enantioselective hydrolysis to provide an optically active form of the compound of formula (XII) and the O-acyl derivative of its antipode.

The racemic compound of formula (XII) is an equimolar mixture of the compound of formula (XIIa)

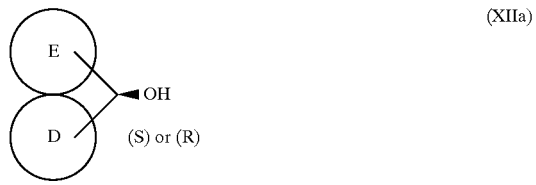

wherein each symbol has the same meaning defined above [hereinafter referred to sometimes as compound (XIIa)] and the compound of formula (XIIb)

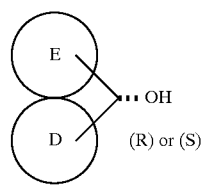

wherein each symbol has the same meaning defined above [hereinafter referred to sometimes as compound (XIIb)]

Both of compound (XIIa) and compound (XIIb) are optically active compounds and the designation (S) or (R) indicates an absolute configuration on the chiral carbon atom.

Compound (XII) can be synthesized by the processes described, cited or inferred in EP 567026, JP Kokai H-6-239843, D. A. Walsh: Synthesis, 677 (1980), and other literature. A typical process is described in Reference Example 1.

The O-acyl derivative of the racemic compound (XII) is a racemic compound of the following formula (XI)

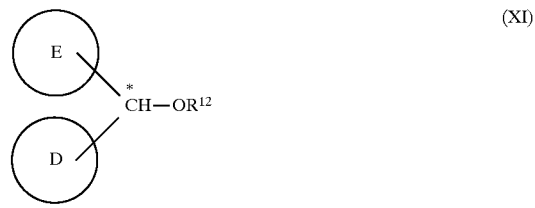

wherein $R^{12}$ represents an acyl group; the other symbols have the same meaning defined hereinbefore. The racemic compound of formula (XI) [hereinafter referred to sometimes as racemic compound (XI)] is an equimolar mixture of the compound of formula (XIa)

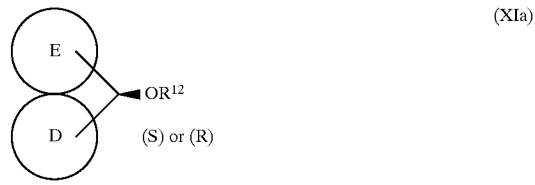

wherein each symbol has the same meaning defined hereinbefore [hereinafter referred to sometimes as compound (XIa)] and the compound of formula (XIb)

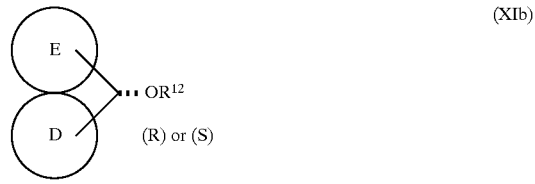

wherein each symbol has the same meaning defined hereinbefore [hereinafter referred to sometimes as compound (XIb).

Both of compound (XIa) and compound (XIb) are optically active. The designations (S) or (R) again indicate an absolute configuration on the chiral carbon atom.

In accordance with this invention, racemic compound (XI) is optically resolved into one optically active form of compound (XII) and the corresponding O-acyl derivative of its antipode.

Thus, racemic compound (XI) undergoes optical resolution to yield either compound (XIIa) and compound (XIb) or compound (XIIb) and compound (XIa).

Referring to the above formulas (XI), (XIa), (XIb), (XII), (XIIa) and (XIIb), the amino group of the "a benzene ring having an unsubstituted or substituted amino group in its 2-position" for ring D may be mono-substituted or di-substituted and in the latter case, the substituents may be the same or different. The substituent group here typically includes acyl, lower($C_{1-6}$)alkyl (e.g. methyl, ethyl, propyl, isopropyl, butyl, isobutyl, sec-butyl, tert-butyl, pentyl, isopentyl, neopentyl, hexyl, isohexyl, etc.) that may be substituted by one to five halogens (e.g. fluorine, chlorine, bromine and iodine), $C_{3-6}$ cycloalkyl (e.g. cyclopropyl, cyclobutyl, cyclopentyl, cyclohexyl, etc.) that may be substituted by one to five halogens (e.g. fluorine, chlorine, bromine and iodine), $C_{6-14}$ aryl (e.g. phenyl, 1-naphthyl, 2-naphthyl, etc.) that may be substituted, and $C_{7-20}$ aralkyl (e.g. benzyl, phenethyl, etc.) that may be substituted. The substituents for $C_{6-14}$ aryl and $C_{7-20}$ aralkyl include one to five substituent(s) selected from the group consisting of (i) halogen atoms (e.g. fluorine, chlorine, bromine and iodine), (ii) $C_{1-4}$ alkyl groups (e.g. methyl, ethyl, propyl and butyl) and (iii) $C_{1-4}$ alkoxy groups (e.g. methoxy, ethoxy, propoxy and butoxy). Preferred is acyl. The acyl mentioned just above includes alkanoyl (e.g. lower $C_{1-6}$ alkylcarbonyl such as acetyl, propionyl, butyryl, isobutyryl, valeryl, isovaleryl, pivaloyl, hexanoyl, etc.) and preferred among them are acetyl and pivaloyl.

In addition to said "unsubstituted or substituted amino group" (hereinafter referred to sometimes as substituent $R^{11}$) in the 2-position, ring D may have at most two substituents, which may be the same or different, in its substitutable positions, such as halogen (e.g. fluorine, chlorine, bromine, iodine), lower($C_{1-4}$)alkyl (e.g. methyl, ethyl, propyl, butyl, tert-butyl, etc.) which may be substituted by one to five halogens (e.g. fluorine, chlorine, bromine and iodine), lower ($C_{1-4}$)alkoxy (e.g. methoxy, ethoxy, propoxy, butoxy, tertbutoxy, etc.) that may be substituted by one to five halogens (e.g. fluorine, chlorine, bromine and iodine), hydroxyl, nitro and cyano. Among them, halogen and lower alkoxy are preferred and halogen (chlorine, in particular) is most advantageous.

Referring, further, to the above formulas (XI), (XIa), (XIb), (XII), (XIIa) and (XIIb), the aromatic ring of said "unsubstituted or substituted aromatic ring" for ring E includes aromatic hydrocarbon groups and heteroaromatic groups, with aromatic hydrocarbon groups being preferred.

Among such aromatic hydrocarbon groups are monocyclic or fused polycyclic $C_{6-14}$ aromatic hydrocarbon groups, such as phenyl, tolyl, xylyl, biphenyl, 1- or 2-naphthyl, 1-, 2- or 9-anthryl, 1-, 2-, 3-, 4- or 9-phenanthryl, 1-, 2-, 4-, 5-, or 6-azulenyl, acenaphthylenyl, etc. Among them, phenyl, 1-naphthyl and 2-naphthyl are preferred and phenyl is more advantageous.

Among the heteroaromatic group mentioned above are 5- to 10-membered, preferably 5- or 6-membered monocyclic heteroaromatic groups containing 1 to 4 hetero atoms selected from atoms of oxygen, sulfur and nitrogen (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.) and fused heteroaromatic groups comprising 2 or 3 of such aromatic hydrocarbon group(s) and heteroaromatic group(s) as mentioned above (e.g. benzofuranyl, isobenzofuranyl, benzo[b]thienyl, indolyl, isoindolyl, 1H-indazolyl, benzimidazolyl, benzoxazolyl, 1,2-benzisooxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo(1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.]. Particularly preferred are furyl, thienyl, indolyl, isoindolyl, pyrazinyl, pyridyl and pyrimidinyl.

The aromatic group represented by ring E may have 1 to 3 (preferably 1 or 2) similar or dissimilar substituents in substitutable positions. Such substituents may for example be halogen (e.g. fluorine, chlorine, bromine, iodine), lower ($C_{1-4}$) alkyl (e.g. methyl, ethyl, propyl, butyl, tert-butyl, etc.) which may be substituted by 1 to 5 halogen(s), lower ($C_{1-4}$)-alkoxy (e.g. methoxy, ethoxy, propoxy, butoxy, tertbutoxy, etc.) which may be substituted by 1 to 5 halogen (s), hydroxyl, nitro and/or cyano. Preferred are halogen (chlorine, in particular), lower($C_{1-4}$)alkoxy (methoxy or ethoxy, in particular) and hydroxyl.

Referring to the above formulas (XI), (XIa) and (XIb), the "acyl" represented by $R^{12}$ includes alkanoyl (e.g. lower $C_{1-6}$ alkylcarbonyl groups such as acetyl, propionyl, butyryl, isobutyryl, valeryl, isovaleryl, pivaloyl, hexanoyl, etc.). Preferred is acetyl.

Preferred species of the compound of formula (XII) are those of formula (IV).

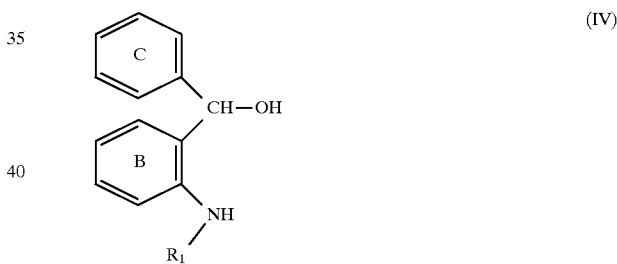

(IV)

wherein the symbols are the same as defined hereinbefore.

Referring to the above formula (IV), ring B, ring C and $R_1$ are exemplified by ring B, ring C and $R_1$ as mentioned in the formula (III) above.

The preferred species of the compounds of formula (XI) and (XII) are those represented by the following formulas (XI') and (XII'), respectively.

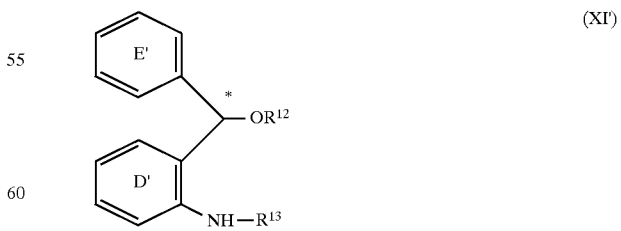

(XI')

wherein $R^{13}$ represents acyl; ring E' represents benzene ring which may be substituted by halogen, lower alkoxy or hydroxyl; ring D' is a benzene ring which may be further substituted by halogen; the other symbols are the same as defined hereinbefore

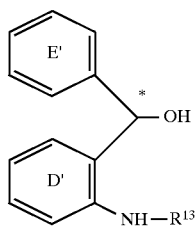

(XII')

wherein each symbol has the same meaning defined above

Referring to the above formulas (XI') and (XII'), the "acyl" represented by $R^{13}$ includes alkanoyl (e.g. lower ($C_{1-6}$)alkylcarbonyl groups such as acetyl, propionyl, butyryl, isobutyryl, valeryl, isovaleryl, pivaloyl, hexanoyl, etc.) and is preferably acetyl or pivaloyl.

In the above formulas (XI') and (XII'), the benzene ring of said "benzene ring which may be substituted by halogen, lower alkoxy or hydroxyl" for ring E' may have 1 to 3 (preferably 1 or 2) identical or different substituents as selected from among halogen, lower alkoxy and hydroxyl (preferably lower alkoxy) in substitutable positions. The halogen may for example be fluorine, chlorine, bromine or iodine. The lower($C_{1-4}$)alkoxy may for example be methoxy, ethoxy, propoxy, butoxy or tert-butoxy (preferably methoxy or ethoxy).

In the above formulas (XI') and (XII'), the "phenyl" represented by ring D' may have one or more halogen atoms, which may be similar or dissimilar, in substitutable positions in addition to the group represented by —$NHR^{13}$. The halogen mentioned just above includes fluorine, chlorine, bromine and iodine and is preferably chlorine.

The following is a partial list of compounds of formula (XI).

α-(2,3-Dimethoxyphenyl)-2-pivaloylamino-5-chlorobenzyl acetate

α-(2,4-Dimethoxyphenyl)-2-pivaloylamino-5-chlorobenzyl acetate

α-(4-Ethoxy-2-methoxyphenyl)-2-pivaloylamino-5-chlorobenzyl acetate

α-(2,3-Dimethoxyphenyl)-2-acetylamino-5-chlorobenzyl acetate

α-(2,4-Dimethoxyphenyl)-2-acetylamino-5-chlorobenzyl acetate

α-(4-Ethoxy-2-methoxyphenyl)-2-acetylamino-5-chlorobenzyl acetate

The reaction from compound (XII) to compound (XI) in this invention can be carried out by the conventional acylation techniques.

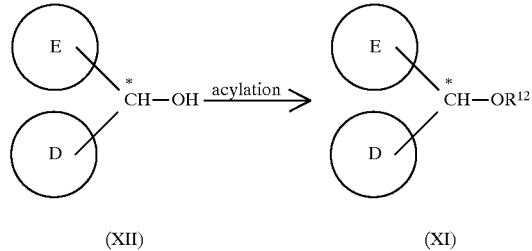

[In the above formulas, each symbol has the same meaning as defined hereinbefore]

By way of illustration, this acylation reaction can be conducted using a suitable acylating agent (e.g. an acid chloride or acid anhydride) in a solvent selected typically from among ethers such as diethyl ether, tetrahydrofuran, dioxane, etc., halogen-containing solvents such as dichloromethane, dichloroethane, chloroform, carbon tetrachloride, etc., hydrocarbons such as benzene, toluene, hexane, heptane, etc., N,N-dimethylformamide, dimethyl sulfoxide, etc., where necessary in the presence of water and a base (e.g. an organic base such as 4-dimethylaminopyridine, triethylamine, triethylenediamine, tetramethylethylenediamine, etc. or an inorganic base such as sodium hydrogen carbonate, potassium hydrogen carbonate, sodium carbonate, potassium carbonate, sodium hydroxide, potassium hydroxide, sodium hydride, potassium hydride, etc.). Based on the compound (XII), the acylating agent and the base are each used in a proportion of generally about 1–10 molar and equivalents preferably about 1–3 molar equivalents. The reaction time is generally about 10 minutes to 24 hours and preferably about 0.5–3 hours. The reaction temperature is generally about 0–100° C. and preferably about 20°–80° C.

In accordance with this invention, the O-acyl derivative [racemic compound (XI)] of a racemic compound (XII) is subjected to enzymatically enantioselective hydrolysis reaction to provide an optically active form of said compound (XII) and the corresponding O-acyl derivative of its antipode. In other words, either compound (XIa) or compound (XIb) in an equimolar mixture of (XIa) and (XIb) (racemic compound) is stereospecifically hydrolyzed enzymatically.

From the reaction mixture obtained in the above manner, the desired optically active form of the compound of formula (XIa), (XIb), (XIIa), or (XIIb) as the case may be can be isolated by known purification procedures such as distillation, solvent extraction, redistribution, crystallization, recrystallization and chromatography (e.g. column chromatography), among other techniques. Moreover, the compound (XIa) or (XIb) so obtained can be hydrolyzed, either chemically or enzymatically, to compound (XIIa) or compound (XIIb) as may be derived.

In accordance with this invention, said enzymatic enantioselective hydrolysis reaction is carried out using a culture broth from a strain of microorganism capable of catalyzing enantioselective hydrolysis, a composition of matter derived from said culture broth, an enzyme of the animal origin (e.g. swine liver esterase, rabbit liver esterase), or an enzyme of the vegetable origin (e.g. wheat germ lipase).

The microorganism capable of catalyzing enantioselective hydrolysis that can be used is not limited as long as it has the ability to enantioselectively hydrolyze the racemic compound (XI) and can be selected from among bacteria, ray fungi and molds. Such bacteria includes for example, those belonging to the genus Pseudomonas or the genus Bacillus. To be specific, *Pseudomonas sp.* S-6, *Pseudomonas sp.* S-11, and *Pseudomonas sp.* S-13, among others, can be mentioned. The above-mentioned *Pseudomonas sp.* S-6, sp. S-11 and sp. S-13 have been deposited with and available from Institute for Fermentation, Osaka (IFO) (Yodogawa-Ku, Osaka) as of Dec. 23, 1994 under the accession numbers of IFO 15786, IFO 15787 and IFO 15788, respectively. Also, they are deposited at National Institute of Bioscience and Human-Technology Agency of Industrial Science and Technology as the International Depositary Authority Ibaraki as accession numbers FERM BP-5205, FERM BP-5206 and FERM BP-5207 respectively on Aug. 24, 1995. As bacteria of the genus Bacillus, *B. subtilis* may be mentioned as a specific example. As a type strain, *Bacillus subtilis* IFO 14117 can be mentioned. *Bacillus subtilis* IFO 14117 is described in the Ninth Edition of List of Cultures, 1992 (published from Institute for Fermentation, Osaka) and available for allotment from the same Institute. As to ray fungi, those of the genus Streptomyces can be typically mentioned. To be specific, *Streptomyces sp.* 121–39 can be mentioned. *Streotomyces sp.* 121–39 has been deposited with Institute for Fermentation, bsaka as of Dec. 23, 1994 under the accession number of IFO 15789 and also with National Institute of Bioscience and Human-Technology Agency of Industrial Science and Technology under the accession number FERM BP-5208, Ibaraki as of Aug. 24, 1995. As regards molds, those of the genus Asperaillus can be mentioned by way of example. The lipase (Lipase AP6) purified from a culture broth of a strain of microorganism belonging to the genus Asperaillus is described in the catalog entitled "Lipase AP" (lipid digestant enzyme) published from Amano Pharmaceutical Co., Ltd. and can be purchased from the same manufacturer.

The microorganisms described above can be used as they are but also may be subjected to mutagenic treatment for enhanced conversion rate and substrate stereospecificity.

The bacteriological characteristics of *Pseudomonas sp.* S-6 (briefly, S-6), *Pseudomonas sp.* S-11 (S-11), *Pseudomonas sp.* S-13 (S-13), and *Streptomyces sp.* 121-39 are now described.

These microorganisms, all isolated from soil samples in Yamagata Prefecture, Japan, were studied in accordance with the manner of disclosure necessary for patent applications in the Examination Standards by Industry, "Applied Microbiological Industry (2nd Revision)" (1993), edited by the Patent Office of Japan and the experimental procedures described in the Classification and Identification of Microorganisms edited and authored by Takeharu Hasegawa (Gakkai Shuppan Center, 1990). The results are described below.

I. Bacteriological characteristics of S-6
A) Morphological characteristics

Observation after 3-day culture on nutrient broth-agar at 24° C. reveals rod-shaped cells sized 0.6–0.8×1.1–2.7 μm, occuring singly or, rarely, in pairs, with rounded ends. Motile. Nonsporogenic.

B) Cultural characteristics

The strain is cultured at 24° C. and observed for 1–14 days.

a. Nutrient broth agar plate: Colonies are yellowish gray~yellowish brown, circular, raised and convex. No surface sheen. Entire margin. No diffusible pigments produced.
  b. Nutrient broth agar slant: Luxuriant matted butyrous growth, light yellowish brown.
  c. Bouillon: Surface growth, forming a cover film. Sediments observed.
  d. Nutrient broth gelatin stab: Good growth at top. Gelatin is liquefied well.
  e. Litmus milk: Litmus is reduced. Milk is peptonized but not coagulated.

C) Physiological characteristics
  a. Gram's stain: –
  b. Nitrate reduction: +
  c. Denitrification:–
  d. MR (methyl red) test: –
  e. VP (Voges-Proskauer) test: –
  f. Indole production: –
  g. Hydrogen sulfide production (lead acetate paper): –
  h. Starch hydrolysis: –
  i. Citrate utilization (Koser, Christensen and Simmons media): +
  j. Utilization of inorganic nitrogen sources
      I) Potassium nitrate: –
      II) Ammonium sulfate: –
  k. Production of pigments (King's A and B and mannitol yeast extract agar): Production of a yellow pigment on King's B and mannitol yeast extract agar media.
      King's A medium: glycerol 10 g, peptone 20 g, magnesium chloride 1.4 g, ammonium sulfate 10 g, agar 15 g, distilled water 1000 ml, pH 7.2
      King's B medium: glycerol 10 g, peptone 20 g, potassium monohydrogen phosphate 1.5 g, magnesium sulfate 1.5 g, agar 15 g, water 1000 ml, pH 7.2
      Mannitol yeast extract agar: peptone 2.5 g, sodium chloride 2.5 g, mannitol 5.0 g, yeast extract 2.5 g, agar 20 g, water 1000 ml, pH 7.0
  l. Urease: –
  m. Oxidase: –
  n. Catalase: +
  o. Ranges for growth
      I) pH: Growth at pH 5.0–8.5; optimum pH for growth 6.0–7.5
      II) Temperature: Growth at 5°–36° C.; optimum temperature for growth 20°–30° C.
  p. Relation to oxygen: aerobic
  q. O–F (oxidative fermentative) test (Hugh Leifson test): oxidative
  r. Production of acid and gas from carbohydrates (shown below in Table 1)

TABLE 1

|  | Acid (peptone water) | Gas (peptone water) | Utilization (Davis) |
|---|---|---|---|
| L-Arabinose | – | – | + |
| D-Xylose | – | – | + |
| D-Glucose | + | – | + |
| D-Mannose | – | – | + |
| D-Fructose | – | – | + |
| D-Galactose | + | – | + |
| Maltose | – | – | – |
| Sucrose | – | – | + |
| Lactose | – | – | ± |
| Trehalose | – | – | + |
| D-Sorbitol | – | – | + |
| D-Mannitol | – | – | + |
| Inositol | – | – | + |
| Glycerol | – | – | + |
| Starch | – | – | ± |

+: positive
±: weakly positive
–: negative s. Acid fastness: –
D) Chemotaxonomic characteristics
  a. G+C (guanine-cytosine) content of the DNA: 66.3 mol %
  b. Intracellular fatty acid analysis: nonpolar 2-hydroxy and 3-hydroxy fatty acids are detected.

The above bacteriological characteristics of S-6 were compared with the taxonomical description in Bergey's Manual of Determinative Bacteriology, 8th ed. and that in Bergey's Manual of Systematic Bacteriology, Volume 1, 1984. Because S-6 is a motile Gram-negative rod which is aerobic and grows at 5° C.–36° C., giving positive catalase and negative oxidase reactions, decomposing sugars oxidatively, showing 66.3 mol % G–C of the DNA, and containing 2-hydroxy. and 3-hydroxy fatty acids within the cell, it was considered to be a microorganism of the genus Pseudomonas. S-6 was accordingly designated as *Pseudomonas sp.* S-6.

II. Bacteriological characteristics of S-11

A) Morphological characteristics

Observation after 3-day culture on nutrient broth agar at 24° C. reveals rod-shaped cells sized 0.9~1.2×1.4~2.8 μm, occurring singly or, rarely, in pairs, with rounded ends. Motile. Nonsporogenic.

B) Cultural characteristics

The strain is cultured at 24° C. and observed for 1–14 days.

a. Nutrient broth agar plate: Colonies are light yellowish gray~light grayish white, circular, raised or convex. No surface sheen. Entire margin. No diffusible pigments produced.

b. Nutrient broth agar slant: Luxuriant matted butyrous growth, light yellowish gray~light grayish white.

c. Bouillon: Surface growth, forming a cover film. Sediments observed.

d. Nutrient broth gelatin stab: Good growth at top. Gelatin is liquefied well.

e. Litmus milk: Litmus is reduced. Milk is peptonized but not coagulated.

C) Physiological characteristics a. Gram's stain: − b. Nitrate reduction: + c. Denitrification: − d. MR (methyl red) test: − e. VP (Voges-Proskauer) test: − f. Indole production: − g. Hydrogen sulfide production (lead acetate paper): − h. Starch hydrolysis: − i. Citrate utilization (Koser, Christensen and Simmons media): + j. Utilization of inorganic nitrogen sources
  I) Potassium nitrate: −
  II) Ammonium sulfate: − k. Production of pigments (King's A and B and mannitol yeast extract agar): No pigment production on any of the media.

King's A medium: glycerol 10 g, peptone 20 g, magnesium chloride 1.4 g, ammonium sulfate 10 g, agar 15 g, distilled water 1000 ml, pH 7.2

King's B medium: glycerol 10 g, peptone 20 g, potassium monohydrogen phosphate 1.5 g, magnesium sulfate 1.5 g, agar 15 g, water 1000 ml, pH 7.2

Mannitol yeast extract agar: peptone 2.5 g, sodium chloride 2.5 g, mannitol 5.0 g, yeast extract 2.5 g, agar 20 g, water 1000 ml, pH 7.0 l. Urease: − m. Oxidase: − n. Catalase: + o. Ranges for growth
  I) pH: Growth at pH 4.2–8.5; optimum pH for growth 6.0–7.5
  II) Temperature: Growth at 10°–33° C.; optimum temperature for growth 15°–28° C.

p. Relation to oxygen: aerobic q. O–F (oxidative fermentative) test (Hugh Leifson test]: oxidative r. Production of acid and gas from carbohydrates (shown below in Table 2)

TABLE 2

|  | Acid (peptone water) | Gas (peptone water) | Utilization (Davis) |
|---|---|---|---|
| L-Arabinose | − | − | + |
| D-Xylose | ± | − | + |
| D-Glucose | + | − | + |
| D-Mannose | + | − | + |
| D-Fructose | ± | − | + |
| D-Galactose | + | − | + |
| Maltose | − | − | ± |
| Sucrose | − | − | + |
| Lactose | − | − | ± |
| Trehalose | − | − | + |
| D-Sorbitol | − | − | + |
| D-Mannitol | − | − | + |
| Inositol | − | − | + |
| Glycerol | − | − | + |
| Starch | − | − | ± |

+: positive
±: weakly positive
−: negative s. Acid fastness: −

D) Chemotaxonomic characteristics a. G+C (guanine-cytosine) content of the DNA: 65.0 mol % b. Intracellular fatty acid analysis: nonpolar 2-hydroxy and 3-hydroxy fatty acids are detected.

The above bacteriological characteristics of S-11 were compared with the taxonomical description in Bergey's Manual of Determinative Bacteriology, 8th ed. and that in Bergey's Manual of Systematic Bacteriology, Volume 1, 1984. Because S-11 is a motile Gram-negative rod which is aerobic and grows at 10° C.–33° C., giving positive catalase and positive oxidase reactions, decomposing sugars oxidatively, showing 65.0 mol % G–C of the DNA, and containing 2-hydroxy and 3-hydroxy fatty acids in the cell, it was considered to belong to the genus Pseudomonas. S-11 was accordingly designated as *Pseudomonas sp.* S-11.

III. Bacteriological characteristics of S-13

A) Morphological characteristics

Observation after 3-day culture on nutrient broth agar at 24° C. reveals rod-shaped cells sized 0.9~1.4×1.4~2.1 μm, occurring singly or, rarely, in pairs, with rounded ends. Motile. Polar flagella. Nonsporogenic.

B) Cultural characteristics

The strain is cultured at 24° C. and observed for 1–14 days.

a. Nutrient broth agar plate: Colonies are light yellowish gray~grayish white, circular, raised or convex. The surface is glistening. Entire margin. No diffusible pigments produced.

b. Nutrient broth agar slant: Luxuriant matted butyrous growth, light grayish white.

c. Bouillon: Surface growth, forming a cover film. Sediments observed.

d. Nutrient broth gelatin stab: Good growth at top. Gelatin is liquefied well.

e. Litmus milk: Litmus is reduced. Milk is peptonized but not coagulated.

C) Physiological characteristics a. Gram's stain: − b. Nitrate reduction: + c. Denitrification: − d. MR (methyl red) test: − e. VP (Voges-Proskauer) test: − f. Indole production: − g. Hydrogen sulfide production (lead acetate paper): − h. Starch hydrolysis: − i. Citrate utilization (Koser, Christensen and Simmons media): + j. Utilization of inorganic nitrogen sources
   I) Potassium nitrate: −
   II) Ammonium sulfate: − k. Production of pigments (King's A and B and mannitol yeast extract agar): No pigment production on any of the media.
   King's A medium: glycerol 10 g, peptone 20 g, magnesium chloride 1.4 g, ammonium sulfate 10 g, agar 15 g, distilled water 1000 ml, pH 7.2
   King's B medium: glycerol 10 g, peptone 20 g, potassium monohydrogen phosphate 1.5 g, magnesium sulfate 1.5 g, agar 15 g, water 1000 ml, pH 7.2
   Mannitol yeast extract agar: peptone 2.5 g, sodium chloride 2.5 g, mannitol 5.0 g, yeast extract 2.5 g, agar 20 g, water 1000 ml, pH 7.0 l. Urease: − m. Oxidase: − n. Catalase: + o. Ranges for growth
   I) pH: Growth at pH 5.0–8.5; optimum pH for growth 6.0–7.5
   II) Temperature: Growth at 10°–35° C.; optimum temperature for growth 20°–30° C.

p. Relation. to oxygen: aerobic q. O–F (oxidative fermentative) test (Hugh Leifson test]: oxidative r. Production of acid and gas from carbohydrates (shown below in Table 3)

TABLE 3

|  | Acid (peptone water) | Gas (peptone water) | Utilization (Davis) |
|---|---|---|---|
| L-Arabinose | − | − | + |
| D-Xylose | ± | − | + |
| D-Glucose | + | − | + |
| D-Mannose | ± | − | + |
| D-Fructose | − | − | + |
| D-Galactose | + | − | + |
| Maltose | − | − | + |
| Sucrose | − | − | + |
| Lactose | − | − | + |
| Trehalose | − | − | + |
| D-Sorbitol | − | − | + |
| D-Mannitol | − | − | + |
| Inositol | − | − | + |
| Glycerol | − | − | + |
| Starch | − | − | + |

+: positive
±: weakly positive
−: negative s. Acid fastness: −

D) Chemotaxonomic characteristics a. G+C (guanine-cytosine) content of the DNA: 65.3 mol % b. Intracellular fatty acid analysis: nonpolar 2-hydroxy and 3-hydroxy fatty acids are detected.

The above bacteriological characteristics of S-13 were compared with the taxonomical description in Bergey's Manual of Determinative Bacteriology, 8th ed. and that in Bergey's Manual of Systematic Bacteriology, Volume 1, 1984. Because S-13 is a motile Gram-negative rod which is aerobic and grows at 10° C.–35° C., giving positive catalase and positive oxidase reactions, decomposing sugars oxidatively, showing a DNA G–C content of 65.3 mol %, and containing 2-hydroxy and 3-hydroxy fatty acids in the cell, it was considered to belong to the genus Pseudomonas. S-13 was accordingly identified as *Pseudomonas sp.* S-13.

IV. Microbiological characteristics of sp. 121-39

The microbiological characteristics of *Streptomyces sp.* 121-39, isolated from a sample of soil in Wakayama Prefecture, were investigated in accordance with the procedure described in International Journal of Systematic Bacteriology 16, 313–340 (1966).

Unless otherwise indicated, the cultural characteristics were observed after incubation at 28° C. for 14 days.

(A) Morphological characteristics

The aerial mycelium develops monopodially from the well elongated and branched vegetative (substrate) mycelium and a chain of spores (usually 10–50 spores) formed at the tip of the serial mycelium is linear or moderately wavy. No whorl formation. The spore is cylindrical (0.5–0.6 dia.× 0.8–1.0 μm) and has a smooth surface.

(B) Cultural characteristics

The degree of growth (G), development and color of aerial mycelium (AM), reverse color (R), and production and color of soluble pigment (SP) on various media are shown below in Table 4. The standard color codes given in parentheses are based on The Color Harmony Manual (4th Ed., 1958) of Container Corporation of America.

TABLE 4

| (a) Sucrose nitrate agar | G: good, light yellowish brown (2ia)<br>AM: sparse, white<br>R: light yeliowish brown (2ga-2ia)<br>SP: none |
|---|---|
| (b) Glucose asparagine agar | G: good, yellowish brown (3ne) ~ dark grayish brown (3ni)<br>AM: moderate, grayish white (3ba) ~ gray (3dc)<br>R: yellowish brown (3ne) ~ dark grayish brown (3ni)<br>SP: none |
| (c) Glycerin asparagine agar | G: good, yellowish gray (2gc) ~ brownish gray (2li)<br>AM: moderate, grayish white (3ba) ~ gray (5fe)<br>R: light brown (2lc) ~ dark grayish brown (3ni)<br>SP: none |
| (d) Starch inorganic salt agar | G: moderate, yellowish gray (2ig)<br>AM: moderate, grayish white (3ba) ~ gray (3dc)<br>R: brownish gray (2li) ~ dark brownish gray (2n)<br>SP: dark brownish gray (2nl) |
| (e) Tyrosine agar | G: good, dark grayish brown (3ni) ~ dark brown (3pl)<br>AM: moderate, grayish white (3cb)<br>R: yellowish brown (3ne) ~ dark brown (3pl)<br>SP: dark brown (3pl) |
| (f) Nutrient agar | G: good, light yellowish brown (2ga) grayish yellow-brown (2ic)<br>AM: none<br>R: light yellowish brown (2ga ~ 2ia)<br>SP: none |
| (g) Yeast extract malt extract agar | G: good, yellowish brown (2ne) ~ brown (2pg)<br>AM: sparse, white ~ grayish white (3ba)<br>R: yellowish gray (2le) ~ dark yellowish brown (3pg)<br>SP: none |

TABLE 4-continued

| | |
|---|---|
| (h) Oatmeal agar | G: good, light brown (21c) |
| | AM: sparse, white ~ grayish white (3ba) |
| | R: light brown (2ic) ~ yellowish brown (2ne) |
| | SP: none |
| (i) Peptone yeast extract iron agar | G: good, yellowish gray (2le) |
| | AM: none |
| | R: yellowish gray (2ie ~ 2le) |
| | SP: none |

(C) Physiological characteristics (a) Temperature range for growth: 11°–41° C.

Optimum temperature range for growth: 24°–29° C.

(b) Nitrate reduction: Positive (c) Gelatin liquefaction: negative (glucose peptone gelatin medium)

(d) Starch hydrolysis: positive (e) Skim milk

Coagulation: negative

Peptonization: positive (f) Melanoid pigment production

Tyrosine agar: positive

Peptone yeast extract iron agar: negative p1 (g) Utilization of carbon sources (Pridham & Gotlieb medium)

| | |
|---|---|
| L-Arabinose: | ++ |
| D-Xylose: | ++ |
| D-Glucose: | ++ |
| D-Fructose: | ++ |
| Sucrose: | ± |
| Inositol: | + |
| L-Rhamnose: | ++ |
| Raffinose: | ++ |
| D-mannitol: | ++ |
| Control: | − |

[Note]
++: Comparatively good growth
+: Growth found
±: Intermediate between + and −
−: No growth (D) Chemotaxonomic characteristics Analysis by the method of Hasegawa et al. (Journal of General Applied Microbiology 2, 319–322 (1983)] revealed that the diaminopimellic acid in the HCl-hydrolysate of the cells was the LL-form.

Judging from the gray color of aerial mycelium, linear or moderately wavy spore chains, smooth spore surface, melanoid pigment production, and the LL-form of diaminopimellic acid, this microorganism obviously belongs to the genus Streptomyces and was, therefore, designated as *Streptomyces sp.* 121–39.

The medium for use in the cultivation of a microorganism capable of inducing chiral hydrolysis may be any medium suitable for growing of the strain. By contacting the O-acyl derivative of racemic compound (XII) with the culture broth obtained as above or a derivative of the culture broth, an optically active form of the compound of formula (XII) and the O-acyl derivative of its antipode can be obtained.

As sources of carbon, the medium may contain glucose, sucrose, maltose, dextrin, starch, glycerol, various oils and fats (e.g. soybean oil, olive oil, etc.), and various fatty acids (e.g. palmitic acid, stearic acid, oleic acid, etc.), among others. The source of nitrogen that can be used includes meat extract, yeast extract, dried yeast, soybean flour, defatted soybean meal, corn steep liquor, peptone, casein, cottonseed meal, urea, ammonium salts (e.g. ammonium sulfate, ammonium chloride, ammonium nitrate, ammonium acetate, etc.), among others. The inorganic salt that can be used includes potassium dihydrogen phosphate, potassium monohydrogen phosphate, sodium dihydrogen phosphate, sodium monohydrogen phosphate, sodium nitrate, magnesium sulfate, calcium carbonate, sodium chloride, and other salts of sodium, potassium, calcium and magnesium. Aside from these salts, salts of iron, manganese, zinc, cobalt, nickel, etc. can also be employed. In addition to the above culture medium components, varieties of amino acids, peptides, vitamins, nucleic acid compounds, etc. can be incorporated. For the purpose of adjusting the pH of the culture medium, inorganic or organic acids and/or bases may be added. As antifoaming agents, various oils and fats, surfactants, etc. can be added in appropriate amounts. The pH of the medium is 5–9 and preferably 6–8.

Cultivation is carried out under stationary cultural conditions or aeration cultural conditions. The incubation temperature is about 20°–45° C., preferably about 28°–37° C. The incubation time is about 10–96 hours, preferably about 16–72 hours.

The "culture broth" used in this method is a fermentation broth obtained by cultivation of any of said microorganisms. The composition of matter derived from the culture broth means any of the cells havested by filtering or centrifuging the culture broth, the filtrate or supernatant obtained similarly, the disrupted cells or cell extract obtainable by sonication, French press processing, alumina ball milling, or treatment with a lytic enzyme, a surfactant, or an organic solvent, and the enzyme preparation purified from said culture filtrate or supernatant or said cell extract by, for example, ammonium sulfate precipitation, ion exchange chromatography, adsorption chromatography, gel permeation chromatography or affinity chromatography. The cells or enzyme immobilized on a celite or other support can likewise be employed.

In accordance with this invention, said optically active substance can be obtained by mixing the substrate O-acyl derivative of racemic compound (XII) with said culture broth or said composition of matter derived therefrom. Where the culture broth obtained by growing any of said microorganisms is employed, the reaction can be carried out by adding the substrate to the culture broth. In this procedure, the substrate can be added to the medium concurrently with inoculation, prior to inoculation, or during the growth phase of the microorganism. The substrate may be directly added to the reaction system but is preferably added after dissolution in an organic solvent (e.g. N,N-dimethylformamide, N,N-dimethylacetamide, dimethyl sulfoxide, ethanol, methanol, toluene, etc.) at a suitable concentration.

Where an enzyme purified from the culture broth is used for the reaction, the enzyme may be dissolved in a suitable solvent (e.g. aqueous sodium chloride solution, phosphate buffer, tris-HCl buffer, etc.) and the solution be submitted to the reaction. In this procedure, too, the substrate may be dissolved in a suitable solvent beforehand. As an alternative procedure, the enzyme may be added to a solution of the substrate in a suitable solvent. In this case, too, the enzyme may be previously dissolved in a suitable solvent. It is also possible to dissolve both the enzyme and the substrate concurrently in a common solvent.

While this reaction can be carried out in aqueous medium, it can be conducted in an organic medium (e.g. toluene, ethyl acetate, isopropyl ether, dichloromethane, etc.) or in a binary phase consisting of an aqueous medium and an organic medium.

The concentration of the starting compound (substrate) in this reaction system is about 0.1–100 mg/ml and preferably about 5–30 mg/ml. The proper amount of the culture broth or composition of matter derived therefrom in terms of moist cell weight is 1–50 mg per ml of the reaction system. The reaction temperature is about 15°–80° C. and preferably about 20°–42° C. The pH is about 4–11 and preferably about 6–9. The reaction time is about 10 minutes to 96 hours and preferably about 1–48 hours. If desired, an organic solvent, a reaction accelerator, an enzyme stabilizer, etc. may be added to the reaction system. This reaction can be conducted under stationary condition, shaking or agitation. Where necessary, the cells or the enzyme may be immobilized on a suitable support and subjected to the reaction in a bioreactor.

The conversion rate from compound (XI) to compound (XII) in the reaction of this invention can be calculated by means of the following equation.

$$\text{Conversion } (\%) = \frac{\text{Compound(XIIa)} + \text{compound(XIIb)}}{\text{Compound(XIa)} + \text{compound(XIb)} + \text{compound(XIIa)} + \text{compound(XIIb)}} \times 100$$

[wherein compound (XIa), compound (XIb), compound (XIIa) and compound (XIIb) represent the amounts of the respective compounds after reaction]

The optical purity (enantiomer excess, % ee) of the product (or the substrate), taking the production of a compound of formula (XIIa) as an example, can be calculated by means of the following equation.

$$\text{Optical purity } (\% \ ee) \frac{\text{Compound(XIIa)} - \text{compound(XIIb)}}{\text{Compound(XIIa)} + \text{compound(XIIb)}} \times 100$$

[where compounds (XIa), (XIb), (XIIa), and (XIIb) have the meanings defined above]

The amounts after reaction of compound (XIa), compound (XIb), compound (XIIa), and compound (XIIb) can be respectively determined typically in the following manner.

The reaction mixture after completion of the reaction is made acidic to acetic acid or the like and a suitable amount (e.g. one volume) of an organic solvent (e.g. ethyl acetate) is added. After stirring, the organic layer is subjected to high performance liquid chromatography (HPLC) using a suitable chiral column (e.g. CHIRALCEL OD) for fractional quantitation of compounds (XIa), (XIb), (XIIa) and (XIIb).

From the reaction mixture obtained by the reaction described hereinbefore, compounds (XIa), (XIb), (XIIa) and (XIIb) can be isolated by per se known procedures such as solvent extraction, redistribution, crystallization, recrystallization and chromatography, among others. Furthermore, the compound (XIa) or (XIb) so obtained can be hydrolyzed, chemically or enzymatically, to compound (XIIa) or (XIIb).

As the representative example, the optically active compound of the formula (IV) mentioned before can be prepared according to the process for preparing the optically active compound of the formula (XII) as described above, The optically active compound obtained by the process of this invention is of value as a synthetic material for drugs and farm chemicals and can be used with advantage for the production of, for example, optically active forms of the plasma cholesterol and/or triglyceride concentration lowering compounds disclosed in, inter aliaa , EP Laid-open No. 567026 and JP Applications Laid-open Nos. 18972/1995, JP Applications 229159/1994, 229160/1994 and 244136/1994. By way of illustration, (3R,5S)-trans-7-chloro-5-(2,3-dimethoxyphenyl)-1-neopentyl-1,2,3,5-tetrahydro-2-oxo-4,1-benzoxazepine-3-acetic acid can be synthesized as described in Reference Example 6.

Specifically, optically active form of the compound represented by the formula (III) can be prepared by using the optically active form of the compound of the formula (IV) as a starting material.

That is, which comprises first reacting the optically active form of the compound of the formula (IV) or a salt thereof with a compound of the formula

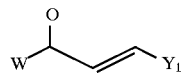

wherein W is a leaving group and $Y_1$ is as defined above, to obtain the optically active form of the compound of the formula (V)

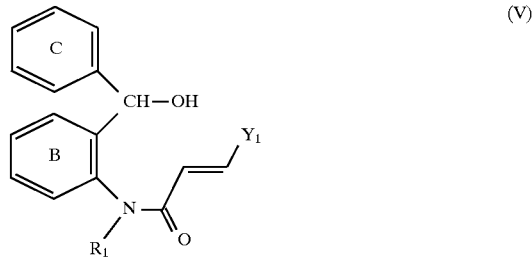

(V)

wherein the symbols are as defined above, or a salt thereof and then subjecting said optically active form of the compound of the formula (V) or a salt thereof to cyclization reaction in the presence of a base.

Referring to the above formulas, the leaving group represented by W includes halogens such as chlorine, bromine and fluorine, preferably chlorine, and $R_1$, ring is B, ring C and $Y_1$ are of the same as those mentioned above for the formula (III).

The process for preparing a 3-carboxyl acid derivative of compound of the formula (III) or corresponding salt which is of value for the prophylaxis or treatment of hyperlipemia can be illustrated below.

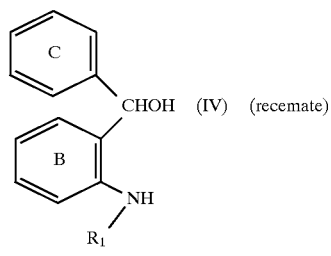
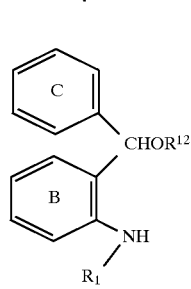
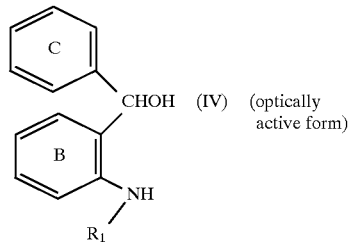
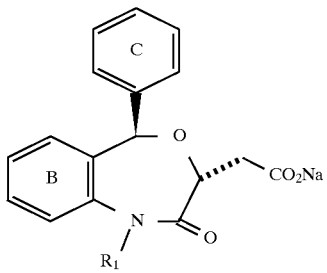
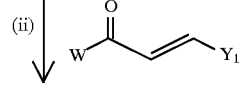
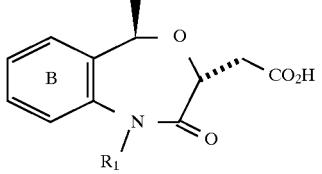
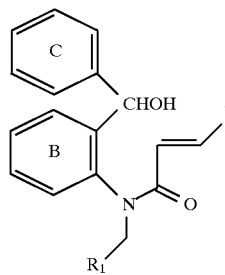
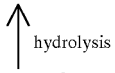
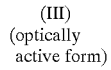
wherein the symbols are of the same meaning as defined above, and the reaction sequences in detail can be carried out according to the description in EPA Laid-open No. 567026.
Among the compound of the formula (IV), particularly the optically active compound of the formula (VI)

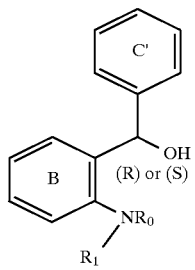

(VI)

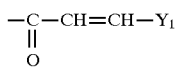

wherein $R_0$ is hydrogen or a group of the formula $$-\underset{\underset{O}{\|}}{C}-CH=CH-Y_1$$

($Y_1$ represents an esterified carboxyl group); $R_1$ is hydrogen or a hydrocarbon group that may be substituted; ring B represents a benzene ring that may be further substituted and ring C' represents a benzene ring having at least a lower alkoxy group and optionally additional substitutuent(s), dissimilar to ring B, are novel and useful intermediate compounds.

Referring to the above formula (VI), ring B, $R_1$ and $Y_1$ are exemplified by the groups mentioned in the formula (III) above. Said lower alkoxy group as the substituted on ring C' includes $C_{1-6}$ alkoxy groups (e.g. methoxy, ethoxy, propoxy, butoxy). Among them, methoxy is preferable. More preference for ring C' is given to the benzene ring having two methoxy groups at 2- and 3-positions or at 2- and 4-positions. Said optionally additional substituents for ring C' are exemplified by the groups mentioned for ring C in the formula (III) above.

Best Mode for Carrying Out the Invention

The present invention is hereinafter described in more detail by means of the following reference examples and examples. These examples exemplify, but do not limit, the present invention, and may be varied, as long as they remain within the scope of the invention.

In the following reference Examples and examples, the term "room temperature" is generally defined as 10° to 30° C. The solvent ratio for purification by silica gel column chromatography is by volume (vol./vol.). The following abbreviations are defined as follows:

s: Singlet
d: Doublet
t: Triplet
m: Multiplet
br: Broad
Hz: Hertz
$CDCl_3$: Heavy chloroform
$CD_3OD$: Heavy methanol
$^1$H-NMR : Proton nuclear magnetic resonance

EXAMPLE 1

*Pseudomonas taetrolens* IFO 12691, *Pseudomonas diminuta* IFO 13182, *Pseudomonas vesicularis* IFO 12165, and *Pseudomonas aeruginosa* IFO 3923 were respectively used to inoculate 20 mL of Trypticase Soy Broth (BBL) in a 200 mL Erlenmeyer flask and shake-cultured at 28° C. for 24 hours. A 0.2 mL portion of the resulting culture was transferred to a 200 mL Erlenmeyer flask containing a casein medium (pH 7.0) composed of 2% glucose, 2.5% casein, 0.1% $KH_2PO_4$, 0.1% $NaNO_3$, and 0.05% $MgSO_4 \cdot 7H_2O$ and shake-cultured at 28° C. for 42 hours. To the resulting culture broth (20 mL) was added 2 mL of a solution of ethyl trans-7-chloro-5-(2-chlorophenyl)-1-neopentyl-2-oxo-1,2,3,5-tetrahydro-4,1-benzoxazepine-3-acetate in dimethyl sulfoxide (10 mg/mL) and the reaction was carried out under shaking at 28° C. for 4.5 hours. After completion of the reaction, 2 mL of the reaction mixture was taken in a test tube, made acidic (pH ca. 4) with 20% acetic acid (40 μl) and diluted with 2 mL of ethyl acetate, followed by stirring. The ethyl acetate layer was appropriately diluted with the HPLC mobile phase (described below) and the resulting dilution was subjected to HPLC using Ultron ES-OUM (Shinwa Chemical Industries, Ltd.) as the chiral column and 20 mM $KH_2PO_4$ (pH 3.5)-acetonitrile (75:25) as the mobile phase for determination of hydrolytic conversion rate, stereospecificity of the reaction, and optical purity of the hydrolysate. The results are shown in Table 5.

The above indicate that each of IFO 13182, IFO 12691 and IFO 12165 hydrolyzed the substrate (racemic compound) stereospecifically to give (3R,5S)-7-chloro-5-(2-chlorophenyl)-1-neopentyl-2-oxo-1,2,3,5-tetrahydro-4,1-benzoxazepine-3-acetic acid and that IFO 3923 hydrolyzed the substrate to give (3S,5R)-7-chloro-5-(2-chlorophenyl)-1-neopentyl-2-oxo-1,2,3,5-tetrahydro-4,1-benzoxazepine-3-acetic acid.

EXAMPLE 2

*Bacillus subtilis* IFO 3026 was used to inoculate a test tube containing 2 mL of N-1 medium (pH 7.2) composed of 1% dextrin, 1% glucose, 1% glycerol, 0.5% polypeptone, 0.5% yeast extract, 0.5% meat extract, 0.3% NaCl, and 0.5% precipitated calcium carbonate. At the same time, 50 μl of a solution of ethyl trans-7-chloro-(2-chlorophenyl)-1-neopentyl-2-oxo-1,2,3,5-tetrahydro-4,1-benzoxazepine-3-acetate in dimethyl sulfoxide (40 mg/mL) was added and the culture and the enzymatic reaction were carried out concurrently under shaking at 28° C. for 48 hours. After completion of the reaction, the reaction mixture was extracted with ethyl acetate and the extract was diluted and subjected to HPLC as in Example 1 for determination of conversion rate, stereospecificity and optical purity. It was found that *Bacillus subtilis* IFO 3026 hydrolyzed the substrate (racemic compound) stereospecifically to give (3S,5R)-7-chloro-5-(2-chlorophenyl)-1-neopentyl-2-oxo-1,2,3,5-tetrahydro-4,1-benzoxazepine-3-acetic acid as shown in Table 5.

TABLE 5

| Microorganism | Conversion (%) | Stereo-specificity | Optical purity (% ee) |
|---|---|---|---|
| *Pseudomonas diminuta* IFO 13182 | 27.8 | 3R, 5S | >99 |
| *Pseudomonas taetrolens* IFO 12691 | 26.7 | 3R, 5S | >99 |
| *Pseudomonas vesicularis* IFO 12165 | 9.0 | 3R, 5S | >99 |
| *Pseudomonas aeruginosa* IFO 3923 | 3.1 | 3R, 5R | >99 |
| *Bacillus subtilis* IFO 3026 | 12.9 | 3R, 5R | >99 |

EXAMPLE 3

*Pseudomonas taetrolens* IFO 12691 was used to inoculate 8 Erlenmeyer flasks (1 L capacity) containing 200 mL of Trypticase Soy Broth (BBL) and shake culture was carried out at 28° C. for 24 hours. About 1.6 liters of the resulting culture was transferred to a 200 L fermenter containing 160 L of casein medium (pH 7.0) composed of 2% glucose, 2.5% casein, 0.1% $KH_2PO_4$, 0.1% $NaNO_3$, and 0.05% $MgSO_4 \cdot 7H_2O$ and aerobic agitation culture was carried out at 28° C. for 42 hours. On the other hand, 200 g of ethyl trans-7-chloro-5-(2,3-dimethoxyphenyl)-1-neopentyl-2-oxo-1,2,3,5-tetrahydro-4,1-benzoxazepine-3-acetate was dissolved in 18 L of dimethyl sulfoxide. This solution was added to 150 L of the above culture broth and the reaction was carried out under agitation at 28° C. for 48 hours. A 2 mL portion of the reaction mixture was taken and extracted with ethyl acetate and the extract was diluted and subjected to HPLC analysis. The conversion rate of the hydrolysis reaction was 44.2% and it was also found that the reaction yielded the (3R,5S) compound with an optical purity of not less than 99% ee.

To the above reaction mixture after completion of the reaction (171 L) was added sodium chloride (17 kg) and the mixture was adjusted to pH 4 with 2N-hydrochloric acid and extracted with 2 portions (80 L and 60 L) of ethyl acetate. The ethyl acetate solutions were combined, washed with 2% aqueous sodium chloride solution (75 L) and 2 portions of 0.5% aqueous sodium hydrogen carbonate solution (15 L each), and concentrated under reduced pressure to provide 295 g of oil. This oil was washed with 2 portions (500 mL and, then, 200 mL) of hexane and suspended in 50% methanol (30 L). The suspension was adjusted to pH 7 with concentrated hydrochloric acid (__mL) and stirred at room temperature for 3 hours. This mixture was filtered through a filter paper and the filtrate was applied to a column of ion exchange resin IRA-68 (1 L, acetate-form, Rohm and Haas Co.). The column was washed with 6 L of 70% methanol and, then, 1N sodium hydroxide/70% methanol was passed through the column to recover 7 L of a crude fraction containing (3R,5S)-7-chloro-5-(2,3-dimethoxyphenyl)-1-neopentyl-2-oxo-1,2,3,5-tetrahydro-4,1-benzoxazepine-3-acetic acid. This fraction was adjusted to pH 4 with concentrated hydrochloric acid (486 mL), diluted with water (3 L), and cooled at 7° C. for 12 hours. This solution was filtered through a filter paper to provide crude crystals (66.7 g) of (3R,5S)-7-chloro-5-(2,3-dimethoxyphenyl)-1-neopentyl-2-oxo-1,2,3,5-tetrahydro-4,1-benzoxazepine-3-acetic acid.

EXAMPLE 4

Ethyl trans-7-chloro-5-(2,4-dimethoxyphenyl)-1-neopentyl-2-oxo-1,2,3,5-tetrahydro-4,1-benzoxazepine-3-acetate, 220 g, was dissolved in 12 L of dimethyl sulfoxide. This solution was added to a culture broth (150 L) of *Pseudomonas taetrolens* IFO 12691 prepared in the same manner as in Example 3 and the reaction was carried out under agitation at 28° C. for 72 hours. Analysis by HPLC revealed that the (3R,5S) compound with an optical purity of not less than 99% ee had been produced at a conversion rate of 43.3%.

The above reaction mixture was purified as in Example 3 to provide crystals (76.1 g) of (3R,5S)-7-chloro-5-(2,4-dimethoxyphenyl)-1-neopentyl-2-oxo-1,2,3,5-tetrahydro-4,1-benzoxazepine-3-acetic acid.

EXAMPLE 5

In 9 L of dimethyl sulfoxide was dissolved 75 g of ethyl trans-7-chloro-5-(4-hydroxy-2-methoxyphenyl)-1-neopentyl-2-oxo-1,2,3,5-tetrahydro-4,1-benzoxazepine-3-acetate. This solution was added to a culture broth (100 L) of *Pseudomonas taetrolens* IFO 12691 prepared in the same manner as in Example 3 and the reaction was carried out at 28° C. for 24 hours. Analysis by HPLC revealed that the (3R,5S) compound with an optical purity of not less than 99% ee had been produced at a conversion rate of 46.8%.

To the above reaction mixture after completion of the reaction (102 L) was added sodium chloride (10 kg) and the mixture was adjusted to pH 4 with 2N hydrochloric acid (2.7 L) and extracted with 2 portions of ethyl acetate (60 L each). The ethyl acetate layers were combined, washed with 2% aqueous sodium chloride solution (70 L) and 2 portions of 1% aqueous sodium hydrogen carbonate solution (35 L each), and concentrated under reduced pressure to provide a concentrate (20 L). This concentrate was back-extracted with 3 portions of 3% aqueous sodium carbonate solution (20 L each) at low temperature (0° C.). The aqueous solutions were pooled, adjusted to pH 7 with 63% sulfuric acid (880 mL), and extracted with 2 portions of ethyl acetate (17.5 L each). The ethyl acetate solutions were combined, washed serially with 2 portions of 0.1N sulfuric acid (17.5 L each) and 2 portions of water (17 L each), and concentrated under reduced pressure to provide an oil (61.1 g). This oil was diluted with sufficient chloroform to make 300 mL and applied to a column of silica gel (500 mL, Kieselgel 60, 70–230 mesh, Merck, Germany). Then, chloroform and chloroform-methanol (20:1) were serially passed through the column. The chloroform-methanol (20:1) eluate gave 3 L of a crude fraction containing (3R,5S)-7-chloro-5-(4-hydroxy-2-methoxyphenyl)-1-neopentyl-2-oxo-1,2,3,5-tetrahydro-4,1-benzoxazepine-3-acetic acid. This fraction was concentrated to dryness and the residue (18.8 g) was dissolved in ethyl acetate and crystallized to provide colorless crystals (14.7 g) of (3R,5S)-7-chloro-5-(4-hydroxy-2-methoxyphenyl)-1-neopentyl-2-oxo-1,2,3,5-tetrahydro-4,1-benzoxazepine-3-acetic acid.

EXAMPLE 6

In 13.5 L of dimethyl sulfoxide was dissolved 200 g of ethyl trans-7-chloro-5-(2-methoxyphenyl)-1-neopentyl-2-oxo-1,2,3,5-tetrahydro-4,1-benzoxazepine-3-acetate. This solution was added to a culture broth (170 L) of *Pseudomonas taetrolens* IFO 12691 obtained in the same manner as in Example 3 and the reaction was carried out at 28° C. for 54 hours. HPLC analysis revealed that the (3R,5S) compound with an optical purity of not less than 99% ee had been produced at a conversion rate of 45%.

To the above reaction mixture after completion of the reaction (71 L) was added sodium chloride (6 kg) and the mixture was adjusted to pH 4 with 2N hydrochloric acid (4.0 L) and extracted with 2 portions of ethyl acetate (60 L each). The ethyl acetate solutions were combined, washed serially with 2% aqueous sodium chloride solution (60 L) and 2 portions of 1% aqueous sodium hydrogen carbonate solution (30 L each), and concentrated under reduced pressure to provide a concentrate (20 L). This concentrate was back-extracted with 4 portions of 3% aqueous sodium carbonate solution (20 L each) at low temperature (0° C.). The aqueous solutions were pooled, adjusted to pH 7 with 63% sulfuric acid (1.9 L), and extracted with 2 portions of ethyl acetate (25 L each). The ethyl acetate solutions were combined, washed serially with 2 portions of 0.1N sulfuric acid (25 L each) and 2 portions of water (25 L each), and concentrated under reduced pressure to provide an oil (136 g). This oil was diluted with sufficient chloroform to make 650 mL and applied to a column of silica gel (1.1 L, Kieselgel 60, 70–230 mesh, Merck, Germany). Then, chloroform and chloroform-methanol (20:1) were serially passed through the column. The chloroform-methanol (20:1) eluate gave 5.5 L of a crude fraction containing (3R,5S)-7-chloro-5-(2-methoxyphenyl)-1-neopentyl-2-oxo-1,2,3,5-tetrahydro-4,1-benzoxazepine-3-acetic acid. This fraction was concentrated to dryness and the residue (114.2 g) was dissolved in ethyl acetate and crystallized to provide colorless crystals (43.8 g) of (3R,5S)-7-chloro-5-(2-methoxyphenyl)-1-neopentyl-2-oxo-1,2,3,5-tetrahydro-4,1-benzoxazepine-3-acetic acid.

EXAMPLE 7

Using a couple of fermenters, *Pseudomonas taetrolens* IFO 12691 was cultured in the same manner as in Example 3 and 400 g of ethyl trans-7-chloro-5-(2,3-dimethoxyphenyl)-1-neopentyl-2-oxo-1,2,3,.5-tetrahydro-4,1-benzoxazepine-3-acetate was added to 300 L of the resulting culture broth. HPLC analysis revealed that the (3R,5S) compound with an optical purity of not less than 99% ee had been produced at a conversion rate of 44.7%.

To the above reaction mixture after completion of the reaction (340 L) was added sodium chloride (34 kg) and the mixture was adjusted to pH 4 with 2N hydrochloric acid (8 L) and extracted with ethyl acetate (170 L). The ethyl acetate solution was washed serially with 2% aqueous sodium chloride solution (100 L) and 2 portions of 0.5% aqueous sodium hydrogen carbonate solution (18 L each), and concentrated under reduced pressure to provide an oil (440 g). This oil was suspended in water (2 L) and washed with hexane (4 L). The hexane was distilled off and the residual aqueous phase was suspended in 50% methanol (to make 12 L). The pH of this 50% methanol suspension was adjusted to 7.88 with 10N-aqueous sodium hydroxide solution (25 mL) and stirred at 30° C. for 3 hours, at the end of which time it was filtered through a filter paper. The filtrate (12 L) was adjusted to pH 4.11 with 6N-hydrochloric acid (61 mL), cooled at 6° C. for 14 hours, and then filtered through a filter paper to provide crude crystals (138.1 g) of (3R,5S)-7-chloro-5-(2,3-dimethoxyphenyl)-1-neopentyl2-oxo-1,2,3,5-tetrahydro-4,1-benzoxazepine-3-acetic acid.

EXAMPLE 8

Using a couple of fermenters, *Pseudomonas* taetrolens IFO 12691 was cultured in the same manner as in Example 3 and 389 g of ethyl trans-7-chloro-5-(2-methoxyphenyl)-1-neopentyl-2-oxo-1,2,3,5-tetrahydro-4,1-benzoxazepine-3-acetate was added to 300 L of the resulting culture broth. HPLC analysis revealed that the (3R,5S) compound with an optical purity of not less than 99% ee had been produced at a conversion rate of 43.5%.

To the above reaction mixture after completion of the reaction (347 L) was added sodium chloride (34.7 kg) and the mixture was adjusted to pH 4 with 2N hydrochloric acid (7.6 L) and extracted with ethyl acetate (173.5 L). The ethyl acetate layer was washed serially with 2% aqueous sodium chloride solution (100 L) and 2 portions of 0.5% aqueous sodium hydrogen carbonate solution (19 L each), and concentrated under reduced pressure to provide an oil (482 g). This oil was washed with 50% methanol (2 L) and the residual solid was suspended in 50% methanol (to make 12 L). This 50% methanol suspension was adjusted to pH 7.86 with 2 N-aqueous sodium hydroxide solution (220 mL) and stirred at 30° C. for 2 hours, at the end of which time it was filtered through a filter paper. The filtrate (12 L) was adjusted to pH 3.86 with 6N-hydrochloric acid (34 mL), cooled at 6° C. for 82 hours, and then filtered through a filter paper to provide crude crystals (134 g) of (3R,5S)-7-chloro-5-(2,3-dimethoxyphenyl)-1-neopentyl-2-oxo-1,2,3,5-tetrahydro-4,1-benzoxazepine-3-acetic acid. The crude crystals were suspended in 60% methanol (2.7 L) and adjusted to pH 8.02 with 10N-sodium hydroxide (29 mL). This suspension was filtered through a glass filter and the filtrate was applied to a column of the adsorbent resin Amberlite XAD-2 (100 mL). The column was irrigated with 60% methanol to recover 3.55 L of a fraction containing (3R,5S)-7-chloro-5-(2,3-dimethoxyphenyl)-1-neopentyl-2-oxo-1,2,3,5-tetrahydro-4,1-benzoxazepine-3-acetic acid. This fraction was adjusted to pH 4.07 with 6N-hydrochloric acid (39 mL), cooled at 6° C. for 6 hours, and filtered through a filter paper to provide crude crystals (115 g) of (3R,5S)-7-chloro-5-(2,3-dimethoxyphenyl)-1-neopentyl-2-oxo-1,2,3,5-tetrahydro-4,1-benzoxazepine-3-acetic acid.

EXAMPLE 9

*Pseudomonas taetrolens* IFO 12691 and *Pseudomonas diminuta* IFO 13182 were respectively cultured in the same manner as in Example 1 to provide culture broths. On the other hand, methyl, ethyl, isopropyl, n-butyl, phenyl and benzyl esters of trans-7-chloro-5-(2-chlorophenyl)-1-neopentyl-2-oxo-1,2,3,5-tetrahydro-4,1-benzoxazepine-3-acetic acid were respectively dissolved in dimethyl sulfoxide at a concentration of 10 mg/mL. A 50 μl portion each of these solutions was added to each of the above culture broths (0.5 mL) and the reaction was carried out under shaking at 28° C. for 16 hours. After completion of the reaction, each reaction mixture was extracted with ethyl acetate and the extract was diluted and analyzed by HPLC. It was found that all the substrates used were asymmetrically hydrolyzed by each of the above culture broths to give (3R,5S)-7-chloro-5-(2-chlorophenyl)-1-neopentyl-2-oxo-1,2,3,5-tetrahydro-4,1-benzoxazepine-3-acetic acid. The hydrolytic conversion rates and the optical purities of the samples of (3R,5S) compound are shown in Table 6.

TABLE 6

| | *Pseudomonas taetrolens* | | *Pseudomonas diminuta* | |
|---|---|---|---|---|
| Ester | Conversion (%) | Optical purity (% ee) | Conversion (%) | Optical purity (% ee) |
| Methyl | 43.6 | >99 | 48.2 | >99 |
| Ethyl | 45.6 | >99 | 45.0 | >99 |
| Isopropyl | 10.4 | >99 | 14.6 | >99 |
| n-Butyl | 4.1 | >99 | 8.9 | >99 |
| Phenyl | 24.7 | >99 | 32.0 | >99 |
| Benzyl | 0.7 | >99 | 6.5 | >99 |

EXAMPLE 10

*Pseudomonas taetrolens* IFO 12691 and *Pseudomonas diminuta* IFO 13182 were respectively cultured in the same manner as in Example 1 to provide culture broths. Ethyl trans-7-chloro-5-(2-chlorophenyl)-1-neopentyl-2-oxo-1,2,3,5-tetrahydro-4,1-benzoxazepine-3-acetate (O-compound) and ethyl trans-7-chloro-5-(2-chlorophenyl)-1-neopentyl-2-oxo-1,2,3,5-tetrahydro-4,1-benzoxazepine-3-acetate (S-compound) were respectively dissolved in dimethyl sulfoxide at a concentration of 10 mg/mL. A 50 μl portion each of these solutions was added to each of the above culture broths (0.5 mL) and the reaction was carried out under shaking at 28° C. for 16 hours. After completion of the reaction, the reaction mixture was extracted with ethyl acetate and the extract was diluted and subjected to HPLC. It was found that all the substrates were asymmetrically hydrolyzed by each of the above culture broths to give the corresponding (3R,5S) compound. The hydrolytic conversion rates and the optical purities of the (3R,5S) compound formed are shown in Table 7.

TABLE 7

|  | Pseudomonas taetrolens | | Pseudomonas diminuta | |
|---|---|---|---|---|
| Substrate | Conversion (%) | Optical purity (% ee) | Conversion (%) | Optical purity (% ee) |
| O | 45.6 | >99 | 45.0 | >99 |
| S | 25.6 | >99 | 21.3 | >99 |

EXAMPLE 11

To 3 mL of Tris-HCl at pH 7.5 were added 240 mg of a lipase derived from Humicola lanuginosa (Biocatalyst Ltd., England) and 3 mg of ethyl trans-7-chloro-5-(2-chlorophenyl)-1-neopentyl-2-oxo-1,2,3,5-tetrahydro-4,1-benzoxazepine-3-acetate and the reaction was conducted at 30° C. for 22.5 hours. The reaction mixture was then extracted with ethyl acetate and the extract was analyzed by HPLC. The analysis revealed that (3R,5S)-7-chloro-5-(2-chlorophenyl)-1-neopentyl-2-oxo-1,2,3,5-tetrahydro-4,1-benzoxazepine-3-acetate (optical purity 94%) had been produced at a conversion rate of 51.2%.

EXAMPLE 12

Using a lipase derived from Rhizopus delemer (Biocatalyst Ltd., England), ethyl trans-7-chloro-5-(2-chlorophenyl)-1-neopentyl-2-oxo-1,2,3,5-tetrahydro-4,1-benzoxazepine-3-acetate was reacted in otherwise the same manner as in Example 11. Analysis of the reaction mixture by HPLC revealed that the corresponding (3R,5S)-compound had been produced at a conversion rate of 32%.

EXAMPLE 13

Pseudomonas diminuta IFO 13182 was cultured in a medium comprising 2% corn steep liquor and 0.1% potassium monohydrogen phosphate (pH 7) at 28° C. for about 28 hours. A 3.2 L portion of the resulting culture was transferred to a 200 L tank fermenter containing 160 L of a medium comprising 2.5%. casein, 0.1% potassium dihydrogen phosphate and 0.05% ammonium sulfate (pH 7) and was further incubated at 28° C. for 48 hours.

In 7 kg of N,N-dimethylformamide was dissolved 300 g of ethyl trans-7-chloro-5-(2,3-dimethoxyphenyl)-1-neopentyl-2-oxo-1,2,3,5-tetrahydro-4,1-benzoxazepine-3-acetate and this solution was added to the culture broth (about 150 L) obtained above. The reaction was carried out under agitation at 24° C. for 71 hours. The reaction mixture was then diluted 40-fold with methanol and the dilution was analyzed by HPLC. The hydrolytic conversion rate was found to be 41.3% and the formation of the (3R,5S)-compound with an optical purity of not less than 99% ee was confirmed.

REFERENCE EXAMPLE 1

α-(2,3-Dimethoxyphenyl)-2-pivaloylamino-5-chlorobenzyl acetate

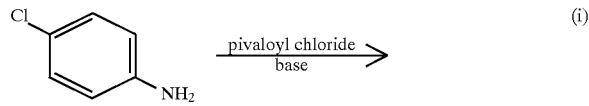

(i)

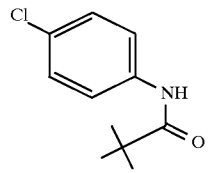

A four-necked flask of 3 L capacity was charged with 225 g (1.764 mol) of p-chloraniline and 450 ml of ethyl acetate and a solution was prepared at 30°–35° C. Then, 500 ml of water and 177.7 g (2.115 mol) of NaHCO$_3$ were added and the mixture was stirred well. To this mixture was added 225 g (1.866 mol) of pivaloyl chloride dropwise at a constant temperature of 30°±5° C. After 1 hour of stirring at the same temperature, 1.35 L of n-hexane was added and the mixture was cooled to 10° C. After 30 minutes of stirring at the same temperature, the crystals (objective compound) that had separated out were harvested by filtration, washed with 500 ml of ethyl acetate-n-hexane (1:4, v/s), and dried under reduced pressure until the crystal crop had reached a constant weight.

Yield 355.4 g (95.2%) IR $v_{max}^{KBr}$ cm$^{-1}$: 3320, 2980, 1660. NMR (CDCl$_3$, 90 MHz) δ: 1.3 (9H, singlet), 7.25 (2H, doublet, J=9 Hz), 7.47 (2H, doublet, J=9 Hz)

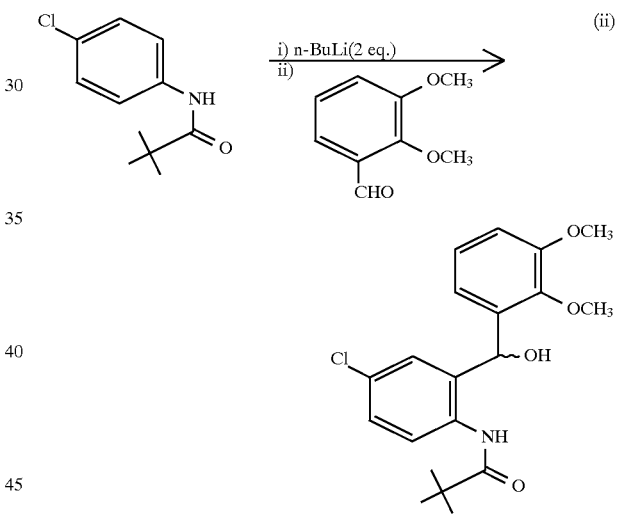

(ii)

Using a four-necked flask of 10 L capacity, 296 g (1.40 mol) of the 4-chloro-N-pivaloylaniline obtained in step (i) was dissolved in 2.22 L of tetrahydrofuran. After the atmosphere in the flask was purged with N$_2$ gas, the flask was cooled to −35° C. Then, 1.85 L (2.96 mol) of 1.6M n-butyllithium(n-BuLi)/n-hexane was added dropwise with constant stirring while the temperature was maintained at −25±10° C. After completion of dropwise addition, the mixture was warmed to 20° C. under stirring and further stirred at this temperature for 2.5 hours. The mixture was then cooled to 0° C. and a solution of 225.7 g (1.54 mol) of 2,3-dimethoxybenzaldehyde in tetrahydrofuran (384 mol) was added dropwise with constant stirring while the temperature was maintained at 0°±3° C. After completion of dropwise addition, the temperature was increased to 20° C. under constant stirring and the mixture was further stirred at that temperature for 1 hour. Then, 780 ml of water was added with stirring while the temperature was maintained at 20°–25° C. The organic (top) layer was separated and washed with 780 ml of 10% aqueous sodium chloride solution twice. The washed organic layer was concentrated under reduced pressure and the residue was stirred in 600 ml of n-hexane at room temperature for 30 minutes. The crystals (objective compound) that had separated out were harvested by filtration, washed with 500 ml of n-hexane-ethyl acetate (4:1, v/v), and dried under reduced pressure until the crystal crop had reached a constant weight.

Yield 390 g (73.8%) IR $v_{max}^{KBr}$ cm$^{-1}$: 3400, 3320, 1650. NMR (CDCl$_3$, 90 MHz) δ: 1.13 (9H, singlet), 3.90 (6H, singlet), 4.28 (1H, doublet, J=4.5 Hz), 6.0 (1H, doublet, J=4.5 Hz), 6.4–8.3 (7H, multiplet), 9.18 (1H, singlet)

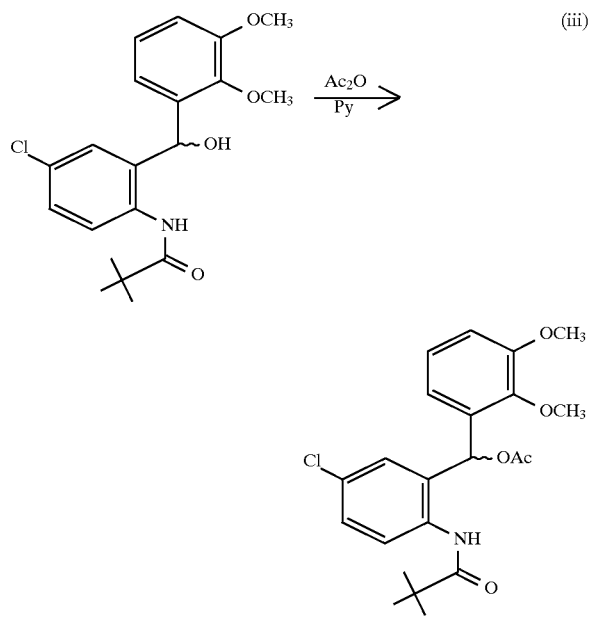

An eggplant-type flask of 2 L capacity was charged with 258 g (0.68 mol) of the α-(2,3-dimethoxyphenyl)-2-pivaloylamino-5-chlorobenzyl alcohol obtained in step (ii), 83.6 g (0.82 mol) of acetic anhydride (Ac$_2$O) and 81 g (1.02 mol) of pyridine (Py) and the mixture was stirred at 70° C. for 3 hours. After cooling, 1.5 L of ethyl acetate, 500 ml of water, and 150 ml of concentrated hydrochloric acid were added and the mixture was stirred well and, then, allowed to stand. The organic layer was taken and washed with 500 ml of water. Then, 26 g of anhydrous MgSO$_4$ and 2.6 g of activated carbon were added and the mixture was stirred for 10 minutes and, then, filtered. The filtrate was washed with 100 ml of ethyl acetate and the filtrate and wash were concentrated under reduced pressure. To this concentrate was added 750 ml of n-hexane under warming and agitation. On cooling to room temperature, a crystal crop of the objective compound separated out. This crop was harvested by filtration, washed with 500 ml of n-hexane, and dried under reduced pressure until the crystal crop had reached a constant weight.

Yield 257.9 g (93.2%) IR $v_{max}^{KBr}$ cm$^{-1}$: 3400, 1720, 1690. NMR (CDCl$_3$, 90 MHz) δ: 1.37 (9H, singlet), 2.17 (3H, singlet), 3.37 (3H, singlet), 3.83 (3H, singlet), 6.8–7.9 (7H, multiplet), 8.93 (1H, singlet)

EXAMPLE 14

Chiral hydrolysis of 2-acetylamino-5-chloro-α-(2-chlorophenyl)benzyl acetate with Lipase AP6

To a mixture of 2-acetylamino-5-chloro-α-(2-chlorophenyl)benzyl acetate (2.0 g), toluene (30 ml), 0.1M potassium dihydrogen phosphate (aq. sol., 20 ml) and 0.1M potassium monohydrogen phosphate (aq. sol., 20 ml) was added Lipase AP6 (Amano Pharmaceutical) (0.8 g) and the whole mixture was stirred vigorously at room temperature for 6 days. To this reaction mixture was added 1N-hydrochloric acid (50 ml) to stop the reaction, followed by extraction with ethyl-acetate (50 ml). The ethyl acetate layer was washed with aqueous sodium hydrogen carbonate solution and dried over anhydrous magnesium sulfate and the solvent was distilled off under reduced pressure. The residue was purified by silica gel column chromatography (hexane:methylene chloride:ethyl acetate=4:1:1–1:1:1). The unreacted 2-acetylamino-5-chloro-α-(2-chlorophenyl) benzyl acetate (1.28 g) was recovered from the first fraction. Then, (S)-2-acetylamino-5-chloro-α-(2-chlorophenyl) benzyl alcohol (0.40 g) was obtained as oil from the second fraction. The optical purity of this product as determined by high performance liquid column chromatography using a chiral column [ULTRON ES-OVM (Shinwa Chemical Industries, Ltd.)] was 85% ee. This (S)-2-acetylamino-5-chloro-α-(2-chlorophenyl)benzyl alcohol of 86 (85)% ee was dissolved in hexane-diethyl ether and the crystals (47 mg) that had separated out were separated. The mother liquor was distilled under reduced pressure to provide (S)-2-acetylamino-5-chloro-α-(2-chlorophenyl)benzyl alcohol of higher purity as oil (0.31 g). Optical purity 96.4% ee.

$[\alpha]_D^{24}$ -65.3° (c=0.48, MeOH)

EXAMPLE 15

Using 4 Erlenmeyer flasks of 200 mL capacity each containing 40 ml of a medium (pH 7.0) composed of 0.5% glucose, 5% dextrin, 3.5% raw soybean flour and 0.7% calcium carbonate, *Streptomyces sp.* 121–39 FERM BP-5208 was shake-cultured at 28° C. for 2 days. The culture thus prepared was transferred in 10 ml aliquots to 15 Erlenmeyer flasks of 1 L capacity each containing 200 ml of the same medium as above and shake culture was carried out at 28° C. for 2 days to prepare 3 L of a culture broth. On the other hand, 3 g of the α-2,3-dimethoxyphenyl-2-pivaloylamino-5-chlorobenzyl acetate (PBH-OAc) obtained in Reference Example 1 was dissolved in 150 ml of N-N-dimethylformamide and the resulting solution was added to the above culture broth (3 L). The reaction was conducted under agitation at 28° C. for 2 days to provide a reaction mixture. A 1 ml portion of this reaction mixture was taken and stirred with 1 ml of ethyl acetate and the top layer was analyzed by HPLC (described above). As a result, the hydrolytic conversion rate was 49% and the optical purity of (S)-5-chloro-α-(2,3-dimethoxyphenyl)-2-pivaloylaminobenzyl alcohol (briefly, (S)-PBH) was 87.7% ee.

REFERENCE EXAMPLE 2

The reaction mixture obtained in Example 2 was extracted with ethyl acetate and 1.96 L of the extract was concentrated under reduced pressure. The residue was purified by flash chromatography using 150 g of silica gel (Wakogel C-300) (eluent=n-hexane:methylene chloride ethyl acetate=6:3:1) (internal pressure 0.2 kg/cm$^2$).

The objective compound-containing fraction was taken and concentrated under reduced pressure. The residue was dissolved in 3 ml of methylene chloride followed by addition of 15 ml of n-hexane and the mixture was allowed to stand overnight. As a result, the objective compound separated out as colorless needles. This crystal crop was harvested by filtration, washed with 10 ml of ethyl acetate-n- hexane (5:1, v/v), and dried under reduced pressure until the crop had reached a constant weight. Crude yield 0.79 g (optical purity 91.8% ee). In 14 ml of methanol was dissolved 0.79 g of the above crystal crop and, then, 0.4 g of activated carbon was added for decolorization. The carbon was filtered off and washed with 10 ml of methanol. The filtrate and wash were combined, warmed to 40° C., diluted with 8 ml of water added portionwise, and allowed to cool and stand in the refrigerator for 3 days. The resulting crystals were collected by filtration and washed with 10 ml of 50% MeOH-H$_2$O and this crop was dried under reduced pressure until it had reached a constant weight. Yield 0.54 g (optical purity 99.2%). This crystal crop was recrystallized from methanol-water (3:1) twice to provide colorless pure needles. Yield 0.124 g (optical purity—100% ee).

The optical purity was determined by HPLC under the following conditions and expressed in enantiomer excess (% ee).

<HPLC conditions>
  Chiral column: CHIRALCEL OD (Daicel Chemical Industries, Ltd.) 4.6 mm×250 mm
  Eluent: n-hexane-iso-PrOH-(9:1, v/v)
  Detection: UV254 nm
  Flow rate: 1.0 ml/min
  Temperature: 25° C.

The pure crystals obtained above were submitted to X-ray crystallographic structure analysis. The absolute configuration of this optically active compound was established as (S) (FIG. 1).

NMR (CDCl$_3$, 90 MHz) δ: 1.37 (9H, singlet), 2.17 (3H, singlet), 3.37 (3H, singlet), 3.83 (3H, singlet), 6.8–7.9 (7H, multiplet), 8.93 (1H, singlet)

REFERENCE EXAMPLE 3

(S)-α-(2,3-Dimethoxyphenyl)-4-chloro-2-(neopentylamino)benzyl alcohol

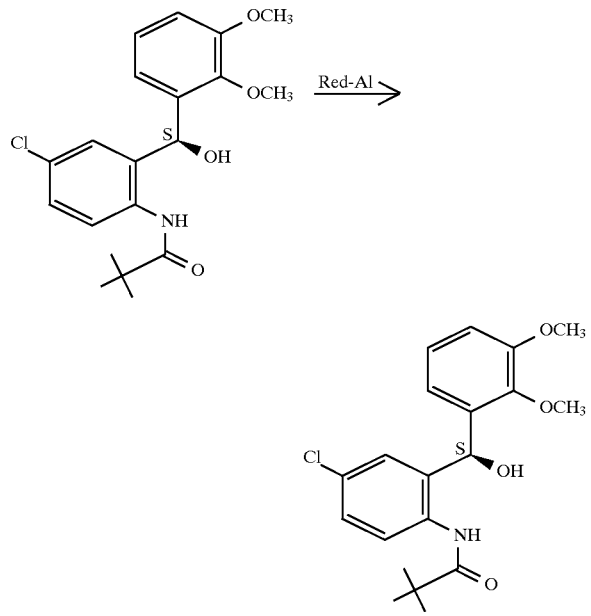

A four-necked flask of 1 L capacity was charged with 60 g (0.159 mol) of (S)-α-(2,3-dimethoxyphenyl)-4-chloro-2-(pivaloylamino)benzyl alcohol, 240 ml of tetrahydrofuran, and 60 ml of methylene chloride and after the atmosphere in the flask was purged with N$_2$ gas, the mixture was stirred with cooling at 10° C. Then, 144 ml of 70% NaAlH$_2$(OCH$_2$CH$_2$OCH$_3$)$_2$ (Red-Al)/toluene maintained at 10–25° C. was added dropwise under constant stirring. After completion of dropwise addition, the mixture was allowed to stand at room temperature overnight. Next morning, 100 ml of water was added dropwise under ice-cooling and stirring and the mixture was extracted with 923 ml of ethyl acetate. The aqueous layer was further extracted with 923 ml of ethyl acetate. The extracts were combined, and 100 g of anhydrous MgSO$_4$ and 6 g of activated carbon powder for decolorization were added. The mixture was stirred for 10 minutes and, then, filtered. The residue on the filter was washed with 462 ml of ethyl acetate. The filtrate and wash were combined and concentrated under reduced pressure. By this procedure, the objective compound was obtained as a viscous oily residue. Crude yield 62.16 g (optical purity 92.9%, yield 99.6%).

IR $v_{max}^{neat}$ cm$^{-1}$: 3430, 2960, 1610, 1590.

REFERENCE EXAMPLE 4

Ethyl trans-3-{N-[4-chloro-2-((S)-α-hydroxy-2,3-dimethoxyphenylmethyl)phenyl]-N-neopentylcarbamoyl}acrylate

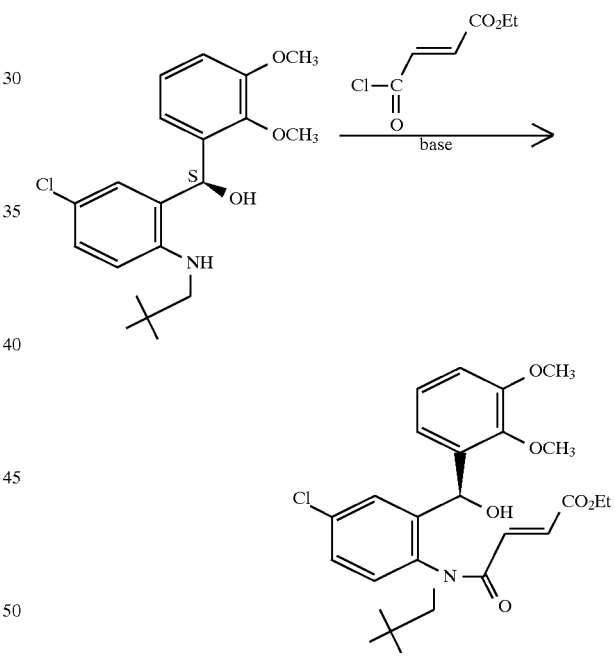

A four-necked flask of 1 L capacity was charged with 57.56 g (1.58 mol) of the (S)-α-(2,3-dimethoxyphenyl)-4-chloro-2-(neopentylamino)benzyl alcohol obtained in Reference Example 3, 347 ml of ethyl acetate, and 238 ml of 1N-NaOH, followed by dropwise addition of 28.4 g (0.175 mol) of monoethyl fumarate chloride with stirring at a constant temperature of 10°–15° C. After completion of dropwise addition, the temperature was increased to 20° C. and the mixture was further stirred for 15 minutes. The organic layer was taken, washed with 400 ml of water, and concentrated under reduced pressure. By this procedure, the objective compound was obtained as a viscous oily residue.

Crude yield 85.65 g (optical purity 90.4%, yield 99.9%)

REFERENCE EXAMPLE 5

Ethyl (3R, 5S)-trans-7-chloro-5-(2,3-dimethoxyphenyl)-1-neopentyl-1,2,3,5-tetrahydro-2-oxo-4,1-benzoxazepine-3-acetate

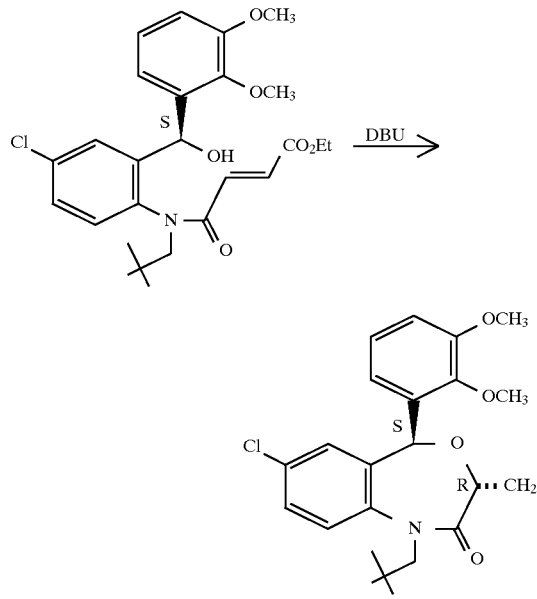

An eggplant-type flask of 1 L capacity was charged with 77.43 g (0.158 mol) of the ethyl trans-3-{N-[4-chloro-2-((S)-α-hydroxy-2,3-dimethoxyphenylmethyl)phenyl]-N-neopentylcarbamoyl}acrylate obtained in Reference Example 4 and 570 ml of ethanol and the flask was heated to dissolve the ester. Then, 29.8 g (0.196 mol) of DBU (1,8-diazabicyclo[5,4,0]-7-undecene) was added and the mixture was refluxed for 2.5 hours. This reaction mixture was gradually cooled to 10° C., whereupon the objective compound separated out as colorless crystals. The crystals were collected by filtration, washed with 180 ml of cold ethanol, and dried under reduced pressure until the crystal crop had reached a constant weight.

Yield 72.91 g (94.2%), mp 158°–159° C.

IR $\nu_{max}^{KBr}$ cm$^{-1}$: 1730, 1680.

REFERMCE EXAMPLE 6

(3R,5S)-trans-7-Chloro-S-(2,3-dimethoxyphenyl)-1-neopentyl-1,2,3,5-tetrahydro-2-oxo-4,1-benzoxazepine-3-acetic acid

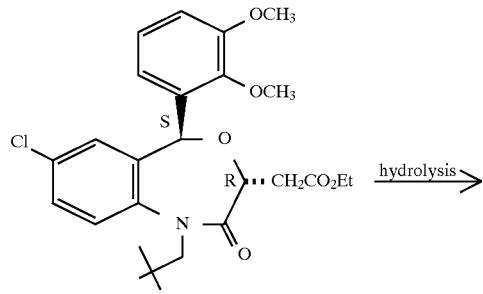

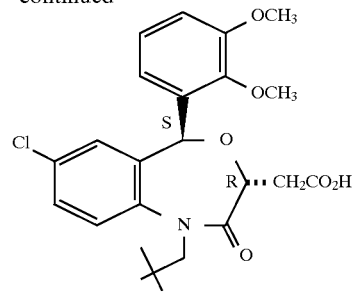

(i) Alkaline hydrolysis

A four-necked flask of 2 L capacity was charged with 70.0 g (0.143 mol) of the ethyl (3R,5S)-trans-7-chloro-5-(2,3-dimethoxyphenyl)-1-neopentyl-1,2,3,5-tetrahydro-2-oxo-4,1-benzoxazepine-3-acetate obtained in Reference Example 5 and 350 ml of tetrahydrofuran. After the ester was dissolved in the solvent, the solution was warmed to 50° C. and 700 ml of ethanol was added. At this temperature, 14.15 g (0.214 mol) of 85% KOH in 70.7 ml of water was added dropwise with stirring. After completion of dropwise addition, the mixture was stirred at the same temperature for 1 hour. After cooling, the reaction mixture was neutralized (pH 7) with about 85 ml of 1N-HCl and, with the internal temperature being maintained at 40°–50° C., the mixture was concentrated under reduced pressure. The residue was diluted with 700 ml of water and concentrated under reduced pressure again to remove the organic solvent. The concentrate was diluted with 700 ml of acetone and adjusted to pH 3 with 160 ml of 1N-HCl. This solution was cooled to 10° C., whereupon the objective compound separated out as crystals. The crystals were collected by filtration, washed serially with 200 ml of 50% (v/v) acetone-water and 200 ml of water, and dried under reduced pressure until the crystal crop had attained a constant weight. The dried crystals were recrystallized from acetone-water (700 ml:700 ml) to provide colorless needles of the objective compound.

Yield 56.1 g (85.0%) (optical purity—100% ee), m.p. 231°–232° C. Elemental analysis for $C_{24}H_{28}NO_6Cl$ (461.94216) Calcd.: C, 62.40; H, 6.11; N, 3.03; Cl, 7.67 Found : C, 62.32; H, 6.09; N, 2.85; Cl, 7.74 IR $\nu_{max}^{KBr}$ cm$^{-1}$: 3650–3350, 3350–3000, 1750, 1660. $[\alpha]_D^{20}$: −268" (c=0.25, CHCl$_3$)

(ii) Acid hydrolysis

An eggplant-type flask of 50 ml capacity was charged with 2.0 g (4 mmol) of the above substrate ethyl ester, 20 ml of dimethoxyethane, and 10 ml of 1N-HCl and the mixture was refluxed for 48 hours. The reaction mixture was then allowed to stand at room temperature for one day, whereupon the objective compound separated out as crystals. This crystal crop was harvested by filtration, washed with 20 ml of 50% (v/v) dimethoxyethane-water, and dried under reduced pressure until the crop had attained a constant weight. Yield 1.3 g (68.9%) (optical purity—100% ee)

The optical purity was determined by high performance liquid chromatography (HPLC) under the following conditions and expressed in enantiomer excess (% ee).

<HPLC conditions>

Chiral column: ULTRON ES-OVM (Shinwa Chemical Industries, Ltd.) 4.6 mm×250 mm

Eluent: 20 mmol $KH_2PO_4$ (aq. sol.) : $CH_3CN$=2000:750 (v/v) (pH 3.5)

Detection: UV 254 nm

Flow rate: 1.0 ml/min.

Temperature: 25° C.

EXAMPLE 16

A 200 mL Erlenmyer flask containing 40 ml of a medium (pH 7.0) composed of 2% sucrose, 2.5% corn steep liquor, 0.1% $KH_2PO_4$, 0.05% ammonium sulfate and 0.5% magnesium sulfate was inoculated with *Bacillus subtilis* IFQ 14117 and incubated under shaking at 28° C. for 1 day. The resulting culture was transferred in 3 ml aliquots to 7 Erlenmyer flasks of 1 L capacity each containing 300 ml of the same medium as above and incubated under shaking at 28° C. for 2 days. The culture broth thus obtained (2.1 L) was centrifuged and the cells were washed with 0.1M Tris-HCl buffer, pH 7.5, and suspended in the same buffer to provide a cell suspension (2.1 L).

In 105 ml of N,N-dimethylformamide was dissolved 4.2 g of PBH-OAc and the solution was added to the above cell suspension (2.1 L). The reaction was carried out under shaking at 28° C. for 1 day to provide a reaction mixture. A 1 ml portion of this reaction mixture was taken and stirred in 1 ml of ethyl acetate and the top layer was analyzed by HPLC. The hydrolytic conversion rate was found to be 49% and the optical purity of (R)-5-chloro-α-(2,3-dimethoxyphenyl)-2-pivaloylaminobenzyl alcohol (briefly, (R)-PBH) was not less than 99% ee.

REFERENCE EXAMPLE 7

The reaction mixture obtained in Example 3 was extracted with ethyl acetate and 2 L of the extract was concentrated under reduced pressure. To the residue was added water and the aqueous supernatant containing water-soluble matter was discarded. The residue was diluted with 100 ml of ethyl acetate and a further amount of water and the ethyl acetate layer was taken. This ethyl acetate layer was concentrated under reduced pressure. The residue was purified by flash chromatography using 60 g of silica gel (Wakogel C-300) (eluent=n-hexane:isopropyl ether:ethyl acetate=7:2:1, v/v). The objective compound-containing fraction was taken and concentrated under reduced pressure to provide crude crystals of the objective compound. Yield 1.5 g (optical purity 99.3% ee). This crude crystal crop, 1.5 g, was dissolved in 30 ml of methanol and decolorized with 0.6 g of activated carbon. The carbon was filtered off and washed with 15 ml of methanol. The filtrate and the wash were combined, diluted with 30 ml of water and allowed to cool and stand in the refrigerator overnight. The crystals that separated out were collected by filtration, washed with 15 ml of 50% methanol/water, and dried under reduced pressure until the crystal crop had reached a constant weight. Yield 0.85 g (optical purity—100% ee).

The optical purity was determined by the procedure described hereinbefore and expressed in enantiomer excess (% ee).

Figure 2:
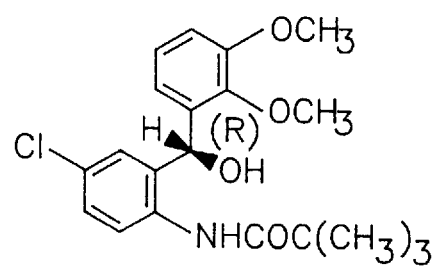
FIG. 2 shows the result of X-ray crystallographic structure analysis.
Figure 2:
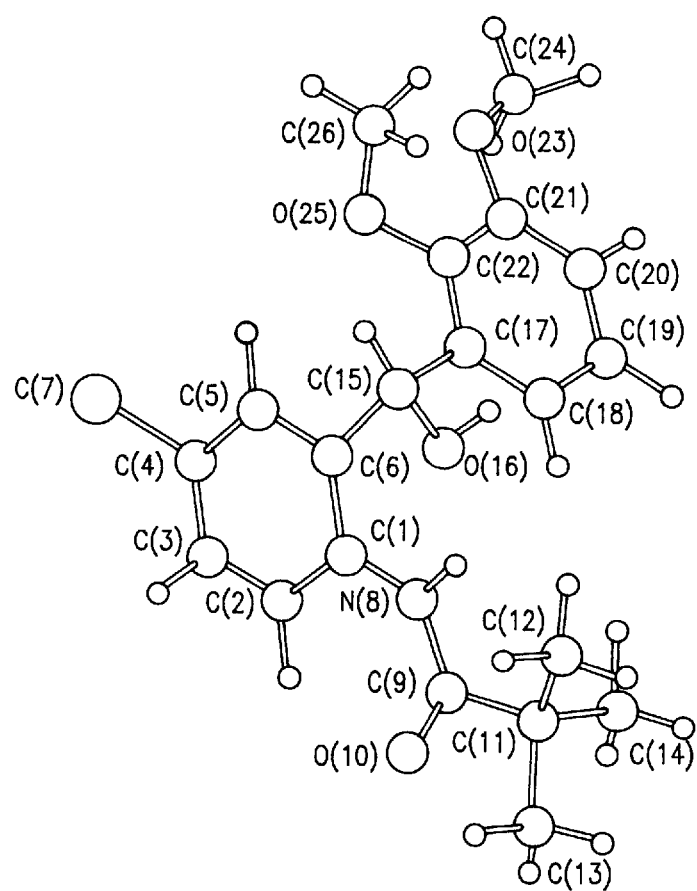

The pure crystal crop obtained above was subjected to X-ray crystallographic analysis. As a result, the absolute configuration of this optically active compound was established as (R) [FIG. 2].

EXAMPLE 17

In a 2 L Sakaguchi flask containing 500 ml of Trypticase Soy Broth [Becton Dickinson, U.S.A.], *Pseudomonas sp.* S-13 FERM BP-5207 was shake-cultured at 28° C. for 1 day. The resulting culture was transferred to a 200 L tank fermenter containing 120 L of a medium (pH 7.0) composed of 2% cottonseed meal, 0.25% $K_2HPO_4$, 0.5% sodium chloride, and 0.25% glucose and aerobic agitation culture was carried out at 28° C. for 2 days. The resulting culture broth, 24 L, was centrifugally concentrated to provide 3 L of a cell suspension.

In 300 ml of methanol was dissolved 30 g of PBH-OAc (Example 15). This solution was added to the above cell suspension (3L) and the reaction was carried out under agitation at 28° C. for 20 hours. After completion of the reaction, a portion of the reaction mixture was extracted with ethyl acetate and the extract was analyzed by HPLC. The hydrolytic conversion rate was 35% and the optical purity of (S)-PBH was not less than 98% ee.

The above reaction mixture (3L) was diluted with an equal volume of ethyl acetate and stirred to give an ethyl acetate solution. This ethyl acetate layer was taken and concentrated under reduced pressure. The residue, 21 g [(S)PBH content 7.03 g (33.45%)], was dissolved in 210 ml of n-hexane:isopropyl ether:ethyl acetate (6:3:1, v/v) and the solution was subjected to flash chromatography [211 g of Wakogel C-300; solvent=n-hexane:isopropyl ether:ethyl acetate=16:3:1, v/v]. The (S)-PBH-containing fraction was taken and concentrated under reduced pressure. To the residue was added 140 ml of n-hexane under warming (50°–60° C.) and the mixture was allowed to cool and stand in the refrigerator overnight. The crystals that separated out were collected by filtration, washed with 50 ml of n-hexane, and dried under reduced pressure until the crystal crop had reached a constant weight. The n-hexane wash was also concentrated under reduced pressure, diluted with 30 ml of n-hexane, and allowed to cool. The crystals that separated out were harvested by filtration, washed with n-hexane, and dried.
Yield 6.73 g.

REFERENCE EXAMPLE 8

Synthesis of α-(2,3-dimethoxyphenyl)-2-pivaloylamino-5-chlorobenzyl alcohol

α-(2,3-Dimethoxyphenyl)-2-pivaloylamino-5-chlorobenzyl alcohol, prepared in Reference Example 1 (ii), can be synthesized by the following alternative process.

(i) Synthesis of N-morpholino-2,3-dimethoxybenzamide

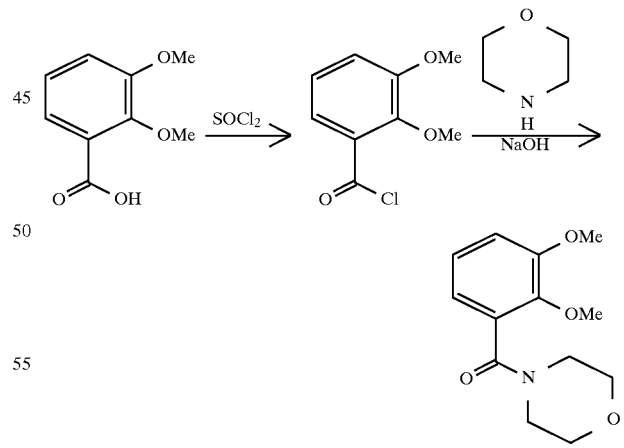

A 200 mL eggplant-type flask was charged with 10 g of 2,3-dimethoxybenzoic acid and 10 ml of thionyl chloride and the mixture was refluxed at 80° C. for 2 hours. The reaction mixture was distilled under reduced pressure and, after addition of 20 ml of methylene chloride, further distilled under reduced pressure. The residue was dissolved in 50 ml of methylene chloride and ice-cooled. After addition of 60 ml of 1N-sodium hydroxide, 5.7 ml of morpholine was added. The mixture was stirred under ice-cooling for 10 minutes and, then, at room temperature for 1 hour. The organic layer was taken and washed serially with 30 ml of 1N-sodium hydroxide, 30 ml of 1N-hydrochloric acid, and 40 ml of water. The organic solvent was distilled off under reduced pressure and the residue was dissolved in 10 ml of methylene chloride. To this solution was added 50 ml of n-hexane dropwise and the crystals that separated out were harvested by filtration. The crystals were washed with 5 ml of n-hexane and dried under reduced pressure to provide 10.2 g of N-morpholino-2,3-dimethoxybenzamide.

Yield 74%. IR $v_{max}^{KBr}$ cm$^{-1}$: 1632 NMR (CDCl$_3$, 300 MHz) δ: 3.18–3.32 (2H, m), 3.58–3.66 (6H, m), 3.87 (3H, s), 3.88 (3H, s), 6.83 (1H, d like), 6.95 (1H, d like), 7.15 (1H, t like)

(ii) Synthesis of 5-chloro-2-pivaloylamino-2',3'-imethoxy benzophenone

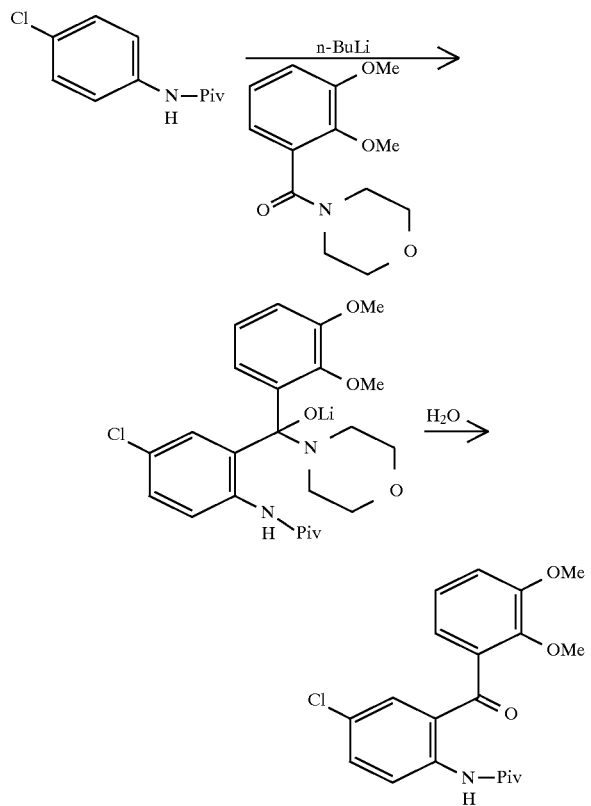

Using a four-necked flask of 50 mL capacity, 2.0 g of N-pivaloyl-p-chloroaniline was dissolved in 10 ml of tetrahydrofuran, and after the atmosphere in the flask was purged with N$_2$ gas, the solution was cooled to –40° C. Then, 12.4 ml of 1.6M n-butyllithium in n-hexane was added dropwise. With the internal temperature being maintained at 25°±5° C., the reaction was conducted with stirring for 2.5 hours. After the internal temperature was reduced to –35° C., a solution of 2.61 g of N-morpholino-2,3-dimethoxybenzamide in 15 ml of tetrahydrofuran was added dropwise under stirring at a constant temperature of –30°±5° C. The internal temperature was then raised to 25±5° C. and the reaction was carried out at that temperature with stirring for 1.5 hours. Then, 5 ml of water was added and the reaction was further carried out with stirring for 20 minutes. The solvent was then distilled off under reduced pressure and the residue was dissolved in 40 ml of methylene chloride. This solution was washed with 30 ml of water twice and the solvent was distilled off under reduced pressure. The residue was dissolved in 2 ml of ethyl acetate followed by addition of 15 ml of n-hexane. The resulting crystals were harvested by filtration, washed with 5 ml of n-hexane, and dried under reduced pressure until the crystal crop had reached a constant weight. By this procedure was obtained 1.61 g of 5-chloro-2-pivaloylamino-2',3'-dimethoxybenzophenone. Yield 45%

IR $v_{max}^{KBr}$ cm$^{-1}$: 3248, 1684, 1642 NMR (CDCl$_3$, 300 MHz) δ6: 1.39 (9H, s), 3.76 (3H, s), 3.93 (3H, s), 6.84–7.52 (1H, d), 8.74–8.82 (5H, m), 11.74 (1H, brs).

(iii) Synthesis of α-(2',3'-dimethoxyphenyl)-2-pivaloylamino-5-chlorobenzyl alcohol

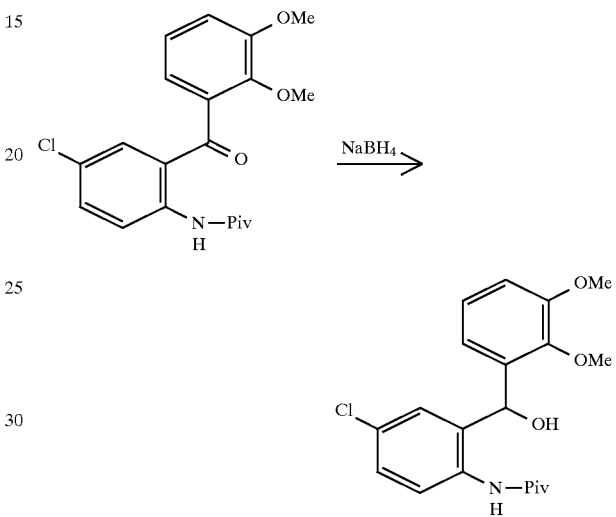

To 100 mg of 5-chloro-2-pivaloylamino-2,3-dimethoxybenzophenone were added 2 ml of ethanol and 0.1 ml of tetrahydrofuran and the mixture was warmed to about 40° C. for dissolution. After the solution was cooled to 25° C., 29 mg of sodium borohydride was added and the reaction was carried out with stirring at 25°–33° C. for 5 hours. The reaction mixture was diluted with 0.1 ml of water and distilled under reduced pressure. The residue was dissolved in 1 mL of methylene chloride and the solution was washed with 1 L of water and distilled under reduced pressure. The residue was dissolved in 0.2 L of methylene chloride followed by addition of 2 mL of n-hexane, whereupon white crystals separated out. The crystals were harvested by filtration, washed with 0.5 mL of n-hexane, and dried under reduced pressure to provide 90.4 mg of 5-chloro-2-pivaloylamino-α-(2',3'-dimethoxyphenyl)benzyl alcohol. Yield 90%.

IR $v_{max}^{KBr}$ cm$^{-1}$: 3404, 3308, 1648 NMR (CDCl$_3$, 90 MHz) δ: 1.13 (9H, s), 3.86 (3H, s), 3.88 (3H, s), 4.36 (1H, d), 6.00 (1H, d), 6.51–6.61 (1H, m), 6.92–7.42 (4H, m), 8.14 (1H, d), 9.19 (1H, b).

EXAMPLE 18

*Pseudomonas sp.* S-13 FERM BP-5207 was shake-cultured in a 500 ml Erlenmeyer flask containing 60 ml of Trypticase Soy Broth (Becton Dickinson, U.S.A.] at 28° C. for 24 hours. The resulting culture was transferred to a 200 l fermenter filled with 120 l of a medium (pH 7.4) containing 2% corn steep liquor, 0.25% dipotassium hydrogen phosphate, 0.5% sodium chloride, 1% sucrose, and an antifoaming agent (q.s.), and incubated under aeration and agitation at 28° C. for 24 hours to prepare a seed culture. A 15 l portion of this seed culture was transferred to a 2000 l fermenter filled with 1500 l of a medium (pH 7.5) containing 2% corn steep liquor, 0.25% dipotassium hydrogen phosphate, 0.5% sodium chloride, 2% sucrose, 3% ammonium sulfate, and an antifoaming agent (q.s.) and incubated under aeration and agitation at 28° C. to provide a fermentation broth.

In 150 l of methanol was dissolved 15 kg of PBH.OAc (described previously). This solution was mixed with the above culture broth and the enzymatic reaction was carried out under stirring at 28° C. for 14 hours. After completion of the reaction, the reaction mixture was analyzed by HPLC. The hydrolytic conversion rate was found to be 44.1% and the optical purities of (S)-PBH and (R)-PBH-OAc were found to be 99% and 96%, respectively. The mixture after completion of the above reaction was transferred from the reaction tank to a different tank and washed with water to obtain 1700 l of a reaction mixture.

EXAMPLE 19

The reaction mixture (1700 l) obtained in Example 5 was subjected to pH 5.0 with sulfuric acid and concentrated to 360 l by means of a ceramic filter with a pore diameter of 0.2 μm (Toshiba Ceramics, Japan). To the concentrate. was added 540 l of ethanol and the mixture was stirred at 50° C. for 1 hour so as to dissolve (S)-PBH. This mixture was maintained at 50° C. and filtered through a ceramic filter with a pore diameter of 0.2 μm (Toshiba Ceramics, Japan). Then, exactly 1800 l of 60% ethanol-water was added and the resulting filtrate, 2370 l, was concentrated to 160 l. To the concentrate was added 6.4 l of Cation PB-40 (NOF Corporation, Japan) and the mixture was extracted with 300 l of ethyl acetate. The ethyl acetate phase was washed serially with 0.1N sulfuric acid, 3% sodium carbonate, and water in that order and, then, concentrated to 63 l. To the concentrate was added 1.2 kg of activated carbon (Shirasagi A, Takeda Chemical Industries, Japan) and the mixture was stirred for 1 hour. The carbon was then filtered off and the filtrate was concentrated. After the residue was diluted with 3 l of ethyl acetate, 103 l of hexane was added for fractional crystallization, whereby 5.6 kg of (S)-PBH crystals were obtained.

EXAMPLE 20

To the mother liquor of fractional crystallization in Example 6 was added a solution of potassium hydroxide (221 g) in methanol (12.3 l) and the hydrolysis reaction was carried out for 30 minutes. This hydrolyzate was crystallized from 24.6 l of water to provide 6.3 kg of crystals composed predominantly of (R)-PBH.

We claim:

1. A process for producing an optically active form of a compound of the formula (IV), which comprises subjecting the O-acyl derivative of a racemic compound of the formula (IV):

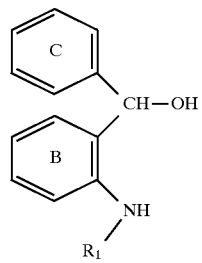

(IV)

wherein $R_1$ represents hydrogen or an alkanoyl group; ring B represents a benzene ring that may be substituted; and ring C represents a benzene ring that may be substituted, and is dissimilar to ring B, or a salt thereof, to enzymatic enantioselective hydrolysis, wherein the hydrolysis is conducted using a microorganism selected from the group of genera consisting of Bacillus, Streptomyces or Pseudomonas, or a culture medium or preparation thereof capable of catalyzing said hydrolysis, or Lipase AP6 to provide an optically active form of said compound of formula (IV) or a salt thereof and the corresponding O-acyl derivative of its antipode.

2. The process of claim 1 wherein said optically active form of the compound of the formula (IV) is isolated.

3. The process of claim 1 wherein the microorganism is Pseudomonas sp. S-6, Pseudomonas sp. S-11 or Pseudomonas sp. S-13.

4. The process of claim 1 wherein said microorganism is Streptomyces sp. 121–39.

5. The process of Claim 1 wherein said microorganism is Bacillus subtilis IFO 14117.

6. The process of claim 1 wherein said microorganisms is from the genus Streptomyces.

7. The process of claim 6 wherein said microorganism of the genus Streptomyces is FERM BP-5208.

8. The process of claim 1 wherein said microorganism of the genus Pseudomonas is a strain selected from the group consisting of FERM BP-5205, FERM BP-5206 and FERM BP-5207.

9. A process for producing an optically active form of a compound of the formula (IV), which comprises subjecting the O-acyl derivative of a racemic compound of the formula (IV):

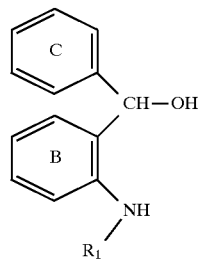

(IV)

wherein $R_1$ represents hydrogen or a hydrocarbon group that may be substituted; ring B represents a benzene ring that may be substituted; and ring C represents a benzene ring that may be substituted, and is dissimilar to ring B, or a salt thereof, to enzymatic enantioselective hydrolysis, wherein the hydrolysis is conducted using a microorganism selected from the group of genera consisting of Bacillus, Streptomyces or Pseudomonas, or a culture medium or preparation thereof capable of catalyzing said hydrolysis, or Lipase AP6 to provide an optically active form of said compound of formula (IV) or a salt thereof and the corresponding O-acyl derivative of its antipode.

* * * * *

UNITED STATES PATENT AND TRADEMARK OFFICE
CERTIFICATE OF CORRECTION

PATENT NO.   : 5,770,438
DATED        : June 13, 1998
INVENTOR(S)  : Kazuo Nakahama et al.

Page 1 of 7

It is certified that error appears in the above-identified patent and that said Letters Patent is hereby corrected as shown below:

TITLE PAGE
ITEM [56] REFERENCES CITED, OTHER PUBLICATIONS

"Hills M et al, BBA 1042:237-240 (1990)." should read --Hills M et al., BBA 1042:237-240 (1990).--.

ITEM [57] ABSTRACT

Line 3, " 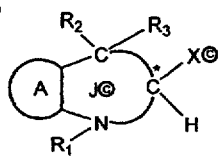 (I)" should read -- 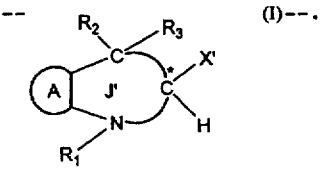 (I)--.

Column 2:
Line 5, " 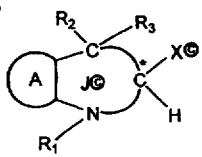 (I)" should read -- 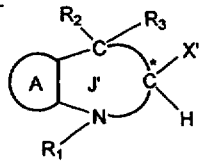 (I)--.

Line 18, "and X'" should read --and X' ,--;

Line 55, " 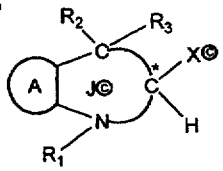 (I)" should read -- 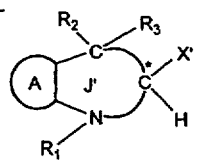 (I)--.

UNITED STATES PATENT AND TRADEMARK OFFICE
CERTIFICATE OF CORRECTION

PATENT NO. : 5,770,438
DATED : June 13, 1998
INVENTOR(S) : Kazuo Nakahama et al.

It is certified that error appears in the above-identified patent and that said Letters Patent is hereby corrected as shown below:

Column 5:
Line 17, comprises should read --comprises:--;
Line 61, "thereof and" should read --thereof; and--.

Column 8:
Line 43, "(4, 3-b]pyridazinyl," should read --[4,3-b]pyridazinyl,--;
Line 45, "nember" should read --member--.

Column 12:
Line 32, "formula (b)" should read --formula (b) ¶ -X-Y$_1$--;
Line 40, "heptamethyiene" should read --heptamethylene--.

Column 13:
Line 31, "lower:" should read --lower--;
Line 44, "memberes" should read --members"--.

Column 14
Line 39, "formula (IA)." should read --formula (IA)--; and
should read

Line 50, "ring J$_1$," should read --ring J$_1$- ;
Line 53, "represents 0 or S)." should read --represents 0 or S.--.

Column 15
Line 11, "formula (III)." should read --formula (III)--.

UNITED STATES PATENT AND TRADEMARK OFFICE
CERTIFICATE OF CORRECTION

PATENT NO. : 5,770,438
DATED : June 13, 1998
INVENTOR(S) : Kazuo Nakahama et al.

It is certified that error appears in the above-identified patent and that said Letters Patent is hereby corrected as shown below:

Column 16:
Line 20, " 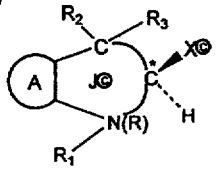 (Ia)" should read -- 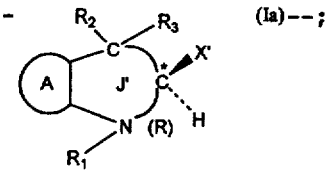 (Ia)--;

Line 28, " 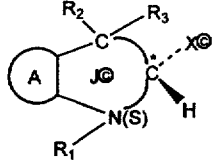 (Ib)" should read -- 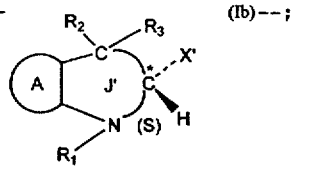 (Ib)--;

Line 35, "hereinbefore" should read --hereinbefore.--;
Line 40, " 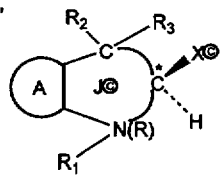 (Iah)" should read -- 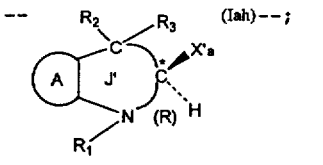 (Iah)--;

Line 49, "formula (Ibh)." should read --formula (Ibh)--;
Line 50, " 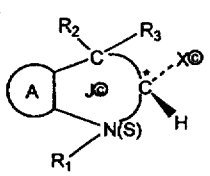 (Ibh)" should read -- 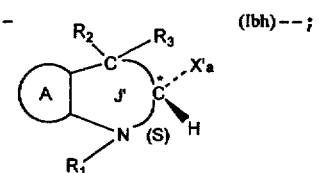 (Ibh)--;

Line 59, "hereinbefore" should read --hereinbefore.--.

UNITED STATES PATENT AND TRADEMARK OFFICE
CERTIFICATE OF CORRECTION

PATENT NO. : 5,770,438
DATED : June 13, 1998
INVENTOR(S) : Kazuo Nakahama et al.

Page 4 of 7

It is certified that error appears in the above-identified patent and that said Letters Patent is hereby corrected as shown below:

Column 17:
Line 5, "microorganisms" should read --microorganism--;
Line 21, "E. vesicularis," should read --P. vesicularis,--;
Line 29, "Osaka)" should read --Osaka))--;
Line 38, [General" should read --(General--;
Line 56, "peptone," should be deleted.

Column 18:
Line 14, "havested" should read --harvested--.

Column 19:
Line 7, " 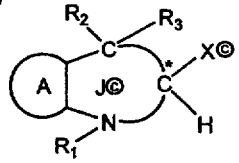 " should read --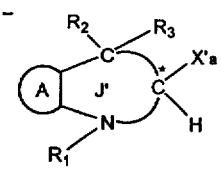--;

Line 25, "reaction" should read --reaction.--.

Column 20:
Line 10, "(XIIb)]" should read --(XIIb)].--.

Column 22:

Line 21, "tertbutoxy," should read --tert-butoxy,--;
Line 32, "(IV)." should read --(IV)--;;
Line 66, "hereinbefore" should read --hereinbefore.--

Column 23:
Line 10, "above,, should read --above.--.

UNITED STATES PATENT AND TRADEMARK OFFICE
CERTIFICATE OF CORRECTION

PATENT NO. : 5,770,438
DATED : June 13, 1998
INVENTOR(S) : Kazuo Nakahama et al.

It is certified that error appears in the above-identified patent and that said Letters Patent is hereby corrected as shown below:

Column 25:
Line 2, "bsaka" should read --Osaka--;
Line 7, "Asperaillus" should read --Aspergillus--;
Line 10, "Asperaillus" should read --Aspergillus--.

Column 26:
Line 24, "(Hugh" should read --[Hugh--.

Column 27:
Line 3, "Observation" should read --¶ Observation--;
Line 63, "(Hugh" should read --[Hugh--.

Column 29:
Line 31, "Relation." should read --Relation--;
Line 32, "(Hugh" should read --[Hugh--.

Column 31:
Line 26, "negative p1", should read --negative-- and "(g)" should read --¶ (g)--;
Line 46, "Microbiology 2," should read --Microbiology 29,--; and "(1983)]" should read --(1983)).

Column 32:
Line 28, "havested" should read --harvested--.

Column 34:
Line 4, "as described above," should read --, as described above.--.

Column 38:
Line 65, "(1 L capacity)" should read --(1L capacity)--.

Column 41:
Line 13, "-OXO-1,2,3,.5-" should read ---OXO-1,2,3,5---;
Line 36, "1-neopentyl2-" should read --1-neopentyl-2---;
Line 60, "2 N-aqueous" should read --2N-aqueous--.

UNITED STATES PATENT AND TRADEMARK OFFICE
CERTIFICATE OF CORRECTION

PATENT NO.   : 5,770,438
DATED        : June 13, 1998
INVENTOR(S)  : Kazuo Nakahama et al.

It is certified that error appears in the above-identified patent and that said Letters Patent is hereby corrected as shown below:

Column 43:
Line 43, "2.5%. casein," should read --2.5% casein,--.

Column 45:
Line 9, "6:1.13" should read --δ:1.13--.

Column 46:
Line 7, "ethyl-acetate" should read --ethyl acetate--;
Line 39, "α-2,3-dimethoxyphenyl)-" should read --α-(2,3-dimethoxyphenyl)---;
Line 58, "chloride" should read --chloride:--.

Column 47:
Line 40,

"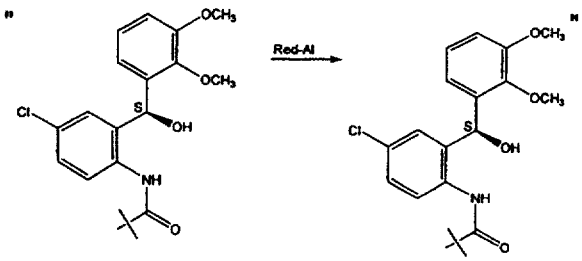"

should read

--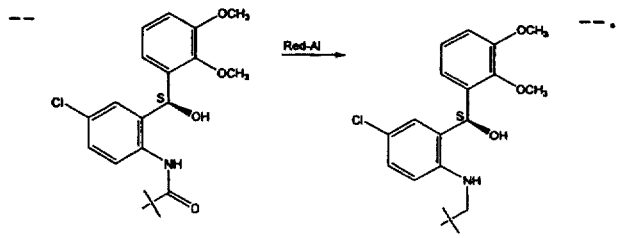--.

UNITED STATES PATENT AND TRADEMARK OFFICE
CERTIFICATE OF CORRECTION

PATENT NO. : 5,770,438
DATED : June 13, 1998
INVENTOR(S) : Kazuo Nakahama et al.

It is certified that error appears in the above-identified patent and that said Letters Patent is hereby corrected as shown below:

Column 48:
Line 26, neopentylcarbamoyllacrylate" should read --neopentylcarbamoyl}acrylate--.

Column 49:
Line 51, "7-Chloro-S-" should read --7-chloro-5---.

Column 51:
Line 2, "Erlenmyer" should read --Erlenmeyer--;
Line 5, "IFQ" should read --IFO--;
Line 8, "Erlenmyer" should read --Erlenmeyer--;
Line 11, "washedwith" should read --washed with--.

Column 52:
Line 37, "2,3-Dimethoxyphenyl)" should read --(2,3-dimethoxyphenyl)--.

Column 54:
Line 10, "δ6:1.39" should read --δ:1.39--;
Line 61, "(Becton" should read --[Becton--.

Column 55:
Line 5, "(q.s.) and" should read --(q.s.), and--;
Line 10, "PBH.OAc" should read --PBH•OAc--;
Line 30, "concentrate." should read --concentrate--.

Signed and Sealed this

Seventh Day of August, 2001

*Attest:*

NICHOLAS P. GODICI
*Attesting Officer*   Acting Director of the United States Patent and Trademark Office